United States Patent [19]
DeLuca

[11] Patent Number: 5,879,934
[45] Date of Patent: *Mar. 9, 1999

[54] HERPES SIMPLEX VIRUS STRAINS FOR GENE TRANSFER

[75] Inventor: Neal A. DeLuca, Cheswick, Pa.

[73] Assignee: University of Pittsburgh of the Commonwealth System of Higher Education, Pittsburgh, Pa.

[ * ] Notice: The term of this patent shall not extend beyond the expiration date of Pat. No. 5,658,724.

[21] Appl. No.: 479,024

[22] Filed: Jun. 7, 1995

Related U.S. Application Data

[63] Continuation-in-part of Ser. No. 342,795, Nov. 21, 1994, which is a continuation of Ser. No. 922,839, Jul. 31, 1992, abandoned.

[51] Int. Cl.$^6$ .................................................. C12N 15/86
[52] U.S. Cl. ..................................... 435/320.1; 536/23.72
[58] Field of Search ........................... 435/172–3, 240–2, 435/320.1, 172.1, 69.1, 172.3, 325, 363, 364, 235.1

[56] References Cited

U.S. PATENT DOCUMENTS 5,026,635  6/1991  Ferguson et al. .
5,070,010  12/1991  Hsu .
5,124,363  6/1992  Temin et al. .

OTHER PUBLICATIONS

DeLuca et al. Isolation and characterization of deletion mutant of Herpes Simplex Virus type 1 in the gene encoding immediate–early regulatory protein ICP4. Journal of Virology. 56(2):558–570, 1985.
Dobson, A. et al., *Nueron*, 5, 353–360 (1990).
Dobson, A. et al., *J. Virol.*, 63, 3844–3851 (1989).
Ho, D.Y and Mocarski, E.S., *Proc. Natl. Acad. Sci. USA*, 86, 7596–7600 (1989).
Lokensgard, J.R. et al., *J. Virol*, 68(11), 7148–58.
Croen et al., *New Eng. J. Med.*, 317(23), 1427–32 (1987).
Batchelor & O'Hare, *J. Virol.*, 64(7), 3269–79 (1990).
Goins et al., *J. Virol.*, 68(4), 2239–52 (1994).
Brakefield & DeLuca, in: *Treatment of Genetic Diseases* (Desnick, ed.), 287–319, Churchill Livingstone (1991).
Brakefield and DeLuca, *The New Biologist*, 3(3), 203–18 (1991).
Chiocca et al., *The New Biologust*, 2(8), 739–46 (1990).
DeLuca & Schafer, *Nucl. Acids. Res.*, 15(11), 4491–4511 (1987).
DeLuca & Schaffer, *J. Virol.*, 62, 732–43 (1988).
DeLuca et al., *J. Virol.*, 56, 558–70 (1985).
Imbalzano et al., *J. Virol.*, 65, 565–74 (1991).
Johnson et al., *J. Virol.*, 68(10), 6347–62 (1994).
Kmetz et al., *Nucl. Acids Res.*, 16(10), 4735 (1988).
McCarthy et al., *J. Virol.*, 63, 18–27 (1989).
Paterson & Everett, *Nucl. Acids Res.*, 16(23), 11005–25 (1988).
Paterson & Everett, *Virol.*, 166, 186 (1988).
Shepard et al., *J. Virol.*, 63, 3714–28 (1989).
Shepard et al., *J. Virol.*, 65, 787–95 (1991).
Shih et al., *Proc. Nat. Acad. Sci. USA*, 81, 5867–70 (1984).
Westruck et al., *J. Virol.*, 64(3), 984–91 (1990).

*Primary Examiner*—David Guzo
*Attorney, Agent, or Firm*—Leydig, Voit & Mayer, Ltd.

[57] ABSTRACT

Cell lines that express complementing levels of herpes simplex virus (HSV) essential immediate early proteins ICP4 and ICP27 and a method of producing the novel cell lines are disclosed. These cell lines are utilized to provide HSV strains deficient for both ICP4 and ICP27, and their generation, and HSV strains deficient for ICP4 and ICP27 and one or more additional genes, and their generation. Vectors are provided from these methods of using these HSV strains for gene transfer and for producing site-specific homologous recombination with cellular DNA.

76 Claims, 11 Drawing Sheets

5,879,934

HERPES SIMPLEX VIRUS STRAINS FOR GENE TRANSFER

This application is a continuation-in-part of U.S. application Ser. No. 08/342,795, filed Nov. 21, 1994, which is a continuation of U.S. application Ser. No. 07/922,839, filed Jul. 31, 1992, now abandoned.

The invention described herein was made in the course of work supported in part by Public Health Service Grant No. AI27431 from the National Institutes of Health, National Institute of Allergies and Infectious Diseases.

1. INTRODUCTION

This invention relates to cell lines that express complementing levels of the herpes simplex virus essential immediate early proteins ICP4 and ICP27, and their generation and use; herpes simplex virus strains deficient for both ICP4 and ICP27, their generation, and use as vectors in various applications including, but not limited to, human gene therapy; herpes simplex virus strains deficient for ICP4 and ICP27 and one or more additional genes, and their generation and use as vectors in various applications including, but not limited to, human gene therapy; novel vectors comprising ICP4$^{(-)}$ICP27$^{(-)}$ HSV strains whose genome contains at least one exogenous gene and an appropriate promoter, and novel vectors comprising ICP4$^{(-)}$ICP27$^{(-)}$ additional HSV gene(s)$^{(-)}$ HSV strains whose genome contains at least one exogenous gene and an appropriate promoter; methods of using the novel HSV strains disclosed herein as vectors; and methods of using the hereinabove cited novel recombinant herpes simplex virus strains to direct homologous recombination with cellular DNA.

2. BACKGROUND OF THE INVENTION

Herpes simplex virus (HSV) contains a double-stranded, linear DNA genome comprised of approximately 152 kbp of nucleotide sequence, which encodes more than 80 genes. The viral genes are transcribed by cellular RNA polymerase II and are temporally regulated, resulting in the transcription and subsequent synthesis of gene products in roughly three discernable phases. These phases, or kinetic classes of genes are referred to as the Immediate Early (IE, or α), Early (E, or β) and Late (L, or γ) genes. Immediately following the arrival of the genome of a virus in the nucleus of a newly infected cell, the IE genes are transcribed. The efficient expression of these genes does not require prior viral protein synthesis. The products of IE genes are required to activate transcription and regulate the remainder of the viral genome.

One IE protein, Infected Cell Polypeptide 4 (ICP4), also known as α4, or Vmw175, is absolutely required for both virus infectivity and the transition from IE to later transcription. Owing to its complex, multifunctional nature and its central role in the regulation of HSV gene expression, ICP4 has been the subject of numerous genetic and biochemical studies. (See DeLuca, et al., 1987, Nucleic Acids Res. 15:4491–4511; DeLuca, et al., 1988, J. Virol. 62:732–743; Paterson, et al., 1988, Virology, 166:186–196; Paterson, et al., 1988, Nucleic Acids Res. 16:11005–11025; Shepard, et al., 1989, J. Virol. 63:3714–3728; and Shepard, et al., 1991, J. Virol. 65:787–795). Aiding in these studies was the development of a system to grow herpes viruses that contain mutations which inactivate essential viral proteins. In this case, cell lines were generated by cotransformation with a plasmid DNA that encoded the neomycin resistance gene from *E. coli* under the control of SV40 early promoter and a plasmid encoding the wild-type ICP4gene. (See DeLuca, et al., 1985, J. Virol. 56:558–570 and DeLuca, et al., 1987, Nucleic Acids Res. 15:4491–4511). These stable cell lines were used to generate and propagate mutant viruses that are void of ICP4 activity. (See DeLuca, et al., 1985, J. Virol. 56:558–570; DeLuca, et al., 1988, J.Virol. 62:732–743; Imbalzano, et al. 1991, J. Virol. 65:565–574; Shepard, et al., 1989, J. Virol., 63:3714–3728, 1989; and Shepard, et al., 1991, J. Virol. 65:787–795). Since the first report of this approach to HSV genetics, numerous studies have followed utilizing this strategy.

From the phenotype of viruses deleted in ICP4, it became evident that such viruses would be potentially useful for gene transfer purposes. Several studies have been published exploring the potential use of such viruses for gene transfer. (See Breakefield, et al., 1991, *Treatment of Genetic Diseases*, Churchill Livingstone, Inc.; and Chocca, et al., 1990, The New Biologist 2:739–746). One property of viruses deleted for ICP4 that makes them desirable for gene transfer is that they only express the five other IE genes: ICP0, ICP6, ICP27, ICP22 and ICP47. (See DeLuca, et al., 1985, J. Virol. 56:558–570). This excludes the expression of viral genes encoding proteins that direct viral DNA synthesis, as well as the structural proteins of the virus. This is desirable from the standpoint of minimizing possible deleterious effects on host cell metabolism following gene transfer.

Despite the fact viruses deleted for ICP4 are blocked at the earliest stage of infection genetically possible subsequent to the delivery of the genome to the host cell nucleus, two phenomena have complicated the use of such viruses for effective gene transfer, or therapy. First, viruses deleted for essential genes, such as ICP4-deficient viruses, require that they are propagated on cultured cells engineered to contain and express the gene deleted from the virus. (See DeLuca, N. A., 1985, J. Virol. 56:558–570). This often results in a subpopulation of viruses that are no longer deleted for that gene due to homologous recombination events between the mutant viral genome and the wild-type gene resident in the host cell genome. (See DeLuca, et al., 1985. J. Virol. 56:558–570). In some cases, this is minimized by deleting from the virus HSV sequences flanking the deleted gene and excluding these sequences from the plasmid used to generate the permissive transformed cell line. Therefore, the gene resident in the transformed cell line does not have flanking nucleotide sequence homology on both sides to promote homologous recombination. This is the case for the ICP4 deletion virus-transformed cell line pair, d120-E5 cells (See DeLuca, et al., 1985, J. Virol. 56:558–570 and DeLuca, et al., 1987, Nucleic Acids Res. 15:4491–4511) and the ICP27 deletion virus-transformed cell line pair, 5 dl 1.2-2-3 cells. (See McCarthy, et al., 1989. J. Virol. 63:18–27).

Secondly, despite only expressing the four other immediate early proteins, ICP4-deficient viruses are toxic to cells in culture and presumably to the majority of cells in an animal. This is most probably due to the expression of one or more of the remaining immediate early proteins and not primarily due to components of the incoming capsid since certain defective HSV virus particles, which contain all the capsid components and none of the IE genes, are not toxic. In addition, ICP4 deficient viruses shutoff host cell protein synthesis through the activity of the UL41 virion gene product (Leib, et al., 1989, J. Virol. 63:759–768; Read, et al., 1993, J. Virol. 67:7149–7160.) The cytotoxicity of ICP4$^{(-)}$ HSV strains is not due to ICP22 and ICP47 and is probably mediated by multiple gene products (Johnson, et al., 1992, J. Virol. 66:2952–2965.)

An HSV mutant virus deficient for the non-essential UL41 gene product is described by Read, et al. (1993, J.

Virol. 67:7149–7160.) No potential use of this UL41$^{(-)}$ HSV mutant as a eukaryotic gene transfer vehicle is suggested by the authors.

HSV ribounucleotide reductase consists of a large (ICP6) and small subunit. Goldstein and Weller (1988, J. Virol. 62:196–205) disclose (1) ribonucleotide reductase activity is not essential for HSV growth, and (2) ICP6 may be inactivated via homologous recombination with a reporter gene (lacZ). The resulting ICP6$^{(-)}$:LacZ$^{(+)}$ HSV strain expresses lacZ and is not dependent upon exogenous ribonucleotide reductase for viral growth. No potential use of this recombinant HSV strain as a gene therapy vehicle is disclosed, taught or suggested.

Therefore, despite attempts to alleviate various problems with use of known HSV mutant strains upon host cell infection, a need exists for defective herpes simplex virus strains that exhibit efficient growth in a controlled laboratory complementing system, a lower level of wild-type virus regeneration and lowered cytotoxic effects.

3. SUMMARY OF THE INVENTION

The present invention provides for novel cell lines which contain DNA encoding for the HSV proteins ICP27 and ICP4. The present invention also provides for a method of producing the novel ICP4$^{(+)}$ICP27$^{(+)}$ cell lines. The method comprises cotransfecting a piece of DNA encoding for ICP27 and a piece of DNA encoding for ICP4 into a suitable cell line and selecting cells which simultaneously harbor both ICP4 and ICP27 encoding DNA. Suitable cell lines include any cell line which will host HSV and which will form colonies. The pieces of DNA encoding ICP27 or ICP4 may be introduced into the cell using any DNA delivery system, such as, for example, retroviral vectors, liposome technology, and recombinant plasmids.

The present invention provides for a method of using the novel ICP4$^{(+)}$ICP27$^{(+)}$ cell lines to produce recombinant HSV strains deficient for both ICP4 and ICP27. The method comprises coinfecting ICP4$^{(+)}$ICP27$^{(+)}$ cells with viruses deficient in ICP4 and viruses deficient in ICP27 and assaying for recombinant ICP4$^{(-)}$ICP27$^{(-)}$ progeny virus.

The present invention provides for the novel recombinant ICP4$^{(-)}$ICP27$^{(-)}$ HSV strains discussed hereinabove. A specific embodiment of the present invention is the ICP4ICP27 complementing cell line, 26 cells.

The present invention also provides a method of efficiently growing the recombinant ICP4$^{(-)}$ICP27$^{(-)}$ HSV strains with an extremely low level of wild-type regeneration. The method comprises infecting ICP4$^{(+)}$ICP27$^{(+)}$ cells with a recombinant ICP4$^{(-)}$ICP27$^{(-)}$ HSV strain and collecting the progeny virus. The inventor has obtained stock titers in excess of $10^9$ plaque forming units (PFU) per milliliter (ml). The frequency of appearance of wild-type recombinant virus in the transformed cell line is calculated at $10^{-12}$. This represents an extremely low ratio of wild-type recombinant to infectious units (PFU).

A specific embodiment of the present invention is d92, a HSV strain deleted for ICP4 and ICP27.

The present invention also provides for novel vectors comprising ICP4$^{(-)}$ICP27$^{(-)}$ HSV strains whose genome contains at least one exogenous gene to be transferred to a cell under the control of the appropriate promoter sequence for purposes including, but not limited to, human gene therapy or the generation of novel cell lines.

The present invention also discloses construction of herpes virus vectors comprising a ICP4$^{(-)}$ICP27$^{(-)}$ background with mutations in additional HSV genes. A novel ICP4$^{(-)}$ICP27$^{(-)}$ HSV strain (and respective complementing cell line as disclosed in this specification) are utilized to construct additional HSV strains which further decrease expressed viral proteins and concomitant deleterious post-infection effects on host cell metabolism.

Therefore, the present invention provides for the novel recombinant ICP4$^{(-)}$ICP27$^{(-)}$ additional HSV gene(s)$^-$ HSV strains. Some of these recombinant ICP4$^{(-)}$ICP27$^{(-)}$ additional HSV gene(s)$^-$ HSV strains will be transcriptionally silent. Many of the genes within the HSV genome are nonessential to virus reproduction in the ICP4ICP27 complementing cell lines. Nonessential genes are those which are nonessential for growth in the ICP4ICP27 complementing cell line. The present invention provides for ICP4$^{(-)}$ICP27$^{(-)}$ additional HSV gene(s)$^-$ HSV strains which are ICP4$^{(-)}$ICP27$^{(-)}$ nonessential HSV gene(s)$^-$ HSV strains.

The present invention also relates to novel recombinant HSV strains deleted for ICP4, ICP27 and the nonessential HSV gene, UL41. The wild type UL41 gene encodes a 58 kD viral tegument protein involved in the virion-host shutoff (vhs) of protein synthesis. UL41 is a late HSV gene product released during host cell infection.

A specific embodiment of the present invention is d33, a HSV strain deleted for ICP4, ICP27 and the non-essential gene, UL41. The d33 genome is approximately 11 kb shorter than wild type HSV.

The present invention also relates to novel recombinant HSV strains deleted for ICP4, ICP27 and the nonessential HSV genes, UL41 and UL39. The nonessential HSV gene UL39 encodes ICP6, the large subunit of ribonucleotide reductase kinase.

Another specific embodiment of the present invention is d94, a HSV strain deleted for ICP4, ICP27, and the non-essential HSV genes UL41 and UL39, with a DNA fragment encoding β-galactosidase inserted within the UL39 coding region. The HSV strain d94 Δ(ICP4:ICP27:UL41:UL39):β-gal expresses β-gal in Vero cells without altering cell morphology as compared to uninfected Vero cells.

d33 and d94 exemplify a central theme of the present invention: UL41 and UL39, alone or in combination, serve as sites of gene inactivation and replacement with a foreign gene of interest so as to generate ICP4$^{(-)}$ICP27$^{(-)}$-based gene transfer vehicles with the improved characteristics enunciated throughout this specification.

The present invention also relates to HSV mutant strains which promote and establish latency within the infected host cell. In one embodiment of the present invention, an HSV strain deficient in at least ICP4 is a preferred candidate for manipulation of the LATs promoter region to increase LATs expression. ICP4$^{(-)}$ strains show a decrease in LATs expression and a concomitant increase in ICP0 expression. Substituting at least a portion of the LAT promoter region (shown to interact in trans with wild type ICP4) with a promoter cassette positively regulated in a ICP4$^{(-)}$ background will increase LAT expression, therefore, (1) helping to promote viral latency within the infected host cell, and (2) inhibiting ICP0 production, the presence of which stimulates host cell lytic infection.

Mutant HSV strains constructed for increased LATs expression are not limited solely to ICP4$^{(-)}$ HSV mutants. In light of the teachings of this specification, any novel HSV mutant strain of the present invention is also a candidate as a template to generate a recombinant HSV vector expressing LATs.

A preferred strategy for construction of a HSV strain exhibiting altered LATs expression is the direct replacement of at least a portion of the wild type LAT promoter region which binds wild type ICP4 in trans with a viral promoter fragment which will be active in the respective HSV mutant genomic background.

In a preferred embodiment of the invention, the HSV strain exhibiting altered LATs expression is d120IELAT. Again, upon review of the teachings of this specification, it will now be within the purview of one of ordinary skill in the art to use any of the disclosed HSV mutant viruses of the present invention as a template to construct an HSV strain exhibiting altered LAT expression. By way of example, and not of limitation, d92 Δ(CP4:ICP27), d33 Δ(ICP4:ICP27: UL41), and d94 Δ(ICP4:ICP27:UL41:UL39):β-gal are candidates for LAT promoter manipulation so as to increase LAT expression. Such a HSV strain will be characterized by reduced expression of viral proteins coupled with increased promotion of latency within the infected cell.

The present invention also discloses the construction and use of ICP27$^{(-)}$ strains containing an additional HSV genomic deletion encoding a partial ICP4 peptide with anomalous biological activity in relation to wild type ICP4 function(s). It is disclosed within this specification that two of the five HSV immediate early gene products, ICP4 and ICP27, have profound effects on viral gene expression and are absolutely essential for virus replication. Data presented within this specification establishes functional interactions between ICP4 and ICP27 that contribute to establishing the program of viral gene expression that ensues during lytic infection.

Therefore, the present invention provides for additional HSV viral mutants, mutants simultaneously deleted for the entire ICP27 coding region and defined functional domains of ICP4. These data, presented in Example Section 12, demonstrate a clear involvement for ICP27 in the induction of early genes, in addition to its known role in enhancing late gene expression during viral infection. In the absence of both ICP4 and ICP27, viral early gene expression, as measured by the accumulation of tk and ICP6 messages was drastically reduced relative to the amounts of these messages seen in the sole absence of ICP4. Therefore, elevated levels of early gene expression as a consequence of ICP27 occurred in the absence of any ICP4 activity. Evidence is also presented regarding the modulation of the ICP4 repression function by ICP27. When synthesized in the absence of ICP27, a mutant ICP4 protein was impaired in its ability to repress transcription from the LS/T promoter in the context of viral infection and in vitro. The defect correlated with the loss of the ability of this mutant protein to bind to its recognition sequence when produced in infected cells in the absence of ICP27. These observations indicate that ICP27 can regulate the activity of at least one domain of the ICP4 protein as well as contribute to elevated early gene expression independent of ICP4. These data provide additional support for the central theme of the present invention: the utilization of novel ICP4$^{(-)}$ICP27$^{(-)}$ HSV mutant genomes for use as vectors.

A particular embodiment of the present invention is an ICP27$^{(-)}$:ICP4 partial peptide mutant containing a deletion of the 3' portion of the ICP4 coding region, from about 800 bp to about 1300 bp of the ICP4 coding region, this region encompassing an ICP4 3' transactivation domain.

A ICP27$^{(-)}$:ICP4 3' transactivation domain partial peptide deletion mutant of the present invention is exemplified, but not limited to, the ICP27$^{(-)}$:ICP4 3' transactivation domain mutant, n208: Δ27.

Another embodiment of the present invention is an ICP27$^{(-)}$:ICP4 partial peptide mutant containing two deletions: a deletion of the 3' portion of the ICP4 coding region, from about 800 bp to about 1300 bp of the ICP4 coding region, and a deletion in the 5' portion of the ICP4 coding region, from about 135 bp to about 200 bp of the ICP4 coding region, this region encompassing an ICP4 5' transactivation domain.

A ICP27$^{(-)}$:ICP4 5'/3' transactivation domain partial peptide deletion mutant of the present invention is exemplified, but not limited to, nd8-10 Δ27.

By using the novel ICP4$^{(+)}$ICP27$^{(+)}$ cell lines and the novel recombinant ICP4$^{(-)}$ICP27$^{(-)}$ HSV strains, the present invention provides methods of producing novel recombinant HSV stains deficient for both ICP4 and ICP27 and also deficient for one or more additional HSV genes.

The present invention provides for methods of efficiently growing the recombinant ICP4$^{(-)}$ICP27$^{(-)}$ nonessential HSV gene(s) HSV strains with an extremely low level of wild-type regeneration. These methods are identical with the methods cited hereinabove for efficiently growing novel recombinant ICP4$^{(-)}$ICP27$^{(-)}$ HSV strains since no proteins encoded by IE genes besides ICP4 and ICP27 are needed for virus replication. The invention provides for novel vectors comprising ICP4$^{(-)}$ICP27$^{(-)}$ HSV strains whose genome contains at least one exogenous gene to be transferred to a cell under the control of an appropriate promoter sequence. The present invention also provides for novel vectors comprising ICP4$^{(-)}$ICP27$^{(-)}$ additional HSV gene(s)$^-$ HSV strains whose genome contains at least one exogenous gene to be transferred to a cell under the control of an appropriate promoter sequence.

The present invention provides for a method of using the hereinabove cited novel HSV strains to direct homologous recombination between cellular sequences cloned into the HSV genome and cellular DNA. The method comprises infecting cells with large amounts of a novel vector, wherein the vector comprises an ICP4$^{(-)}$ICP27$^{(-)}$ HSV strain whose genome contains a gene homologous to a gene existing within the cells or wherein the vector comprises an ICP4$^{(-)}$ ICP27$^{(-)}$ additional HSV gene(s)$^-$ HSV strain whose genome contains a gene homologous to a gene existing within the cells.

It is an object of the present invention to provide novel cell lines which contain DNA encoding for the HSV proteins ICP27 and ICP4.

It is a further object of the present invention to provide a method for producing ICP4$^{(+)}$ICP27$^{(+)}$ cell lines.

It is a further object of the present invention to provide a method of using ICP4$^{(+)}$ICP27$^{(+)}$ cell lines to produce HSV strains deficient for the genes encoding the HSV proteins ICP4 and ICP27.

It is a further object of the present invention to provide novel ICP4$^{(-)}$ICP27$^{(-)}$ HSV strains.

It is a further object of the present invention to provide a method of growing ICP4$^{(-)}$ICP27$^{(-)}$ HSV strains using ICP4$^{(+)}$ICP27$^{(+)}$ cell lines.

It is a further object of the present invention to provide ICP4$^{(-)}$ICP27$^{(-)}$ additional HSV gene(s)$^-$ HSV strains.

It is a further object of the present invention to provide ICP4$^{(-)}$ICP27$^{(-)}$ additional HSV gene(s)$^-$ HSV strains deficient in the HSV UL41 gene.

It is a further object of the present invention to provide ICP4$^{(-)}$ICP27$^{(-)}$ additional HSV gene(s)$^-$ HSV strains deficient in the HSV UL39 gene.

It is a further object of the present invention to provide ICP4$^{(-)}$ICP27$^{(-)}$ additional HSV gene(s)$^-$ HSV strains deficient in the HSV UL41 gene and the HSV UL39 gene.

It is a further object of the present invention to provide ICP4$^{(-)}$ICP27$^{(-)}$ additional HSV gene(s)$^-$ HSV strains as gene transfer vectors, with a foreign DNA fragment(s) inserted within the coding region of said additional HSV gene(s)$^-$.

It is another object of the present invention to provide mutant HSV strains which promote and establish viral latency within the infected host cell.

It is yet another object of the present invention to provide mutant HSV strains which exhibit various phenotypes within the infected cell based on the biological activity of HSV mutant genes expressing a partial peptide.

It is a further object of the present invention to provide a method of producing ICP4$^{(-)}$ICP27$^{(-)}$ additional HSV gene(s)$^-$ HSV strains using ICP4$^{(+)}$ICP27$^{(+)}$ cell lines.

It is a further object of the present invention to provide a method of growing ICP4$^{(-)}$ICP27$^{(-)}$ additional HSV gene(s)$^-$ HSV strains using ICP4$^{(+)}$ICP27$^{(+)}$ cell lines.

It is a further object of the present invention to provide novel vectors comprising ICP4$^{(-)}$ICP27$^{(-)}$ HSV strains whose genome contains at least one exogenous gene to be transferred to a cell under the control of an appropriate promoter sequence.

It is a further object of the present invention to provide novel vectors comprising ICP4$^{(-)}$ICP27$^{(-)}$-additional HSV gene(s)$^-$ HSV strains whose genome contains at least one exogenous gene to be transferred to a cell under the control of an appropriate promoter sequence.

It is a further object of the present invention to provide a method of using the novel HSV strains disclosed as vectors.

It is a further object of the present invention to provide a method of using the disclosed novel HSV strains to direct homologous recombination between cellular sequences cloned into the HSV genome and cellular DNA.

These and other objects of the invention will be more fully understood from the following description of the invention with reference to the figures incorporated herein as a part to this application.

4. BRIEF DESCRIPTION OF THE FIGURES

Figure 5:
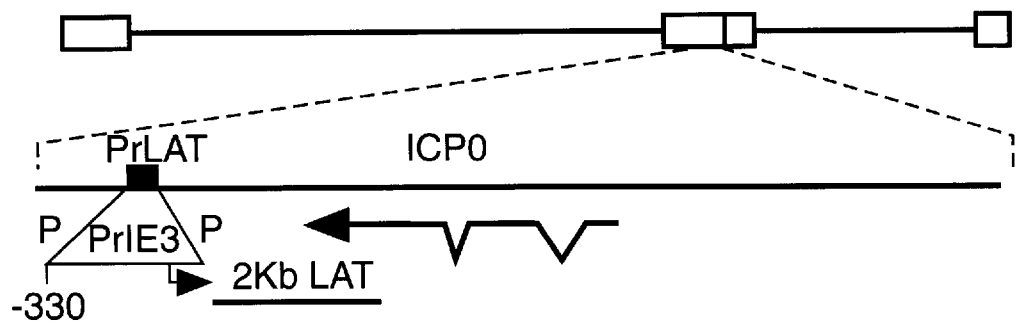

FIG. 5 shows the LAT/ICP0 region of the HSV genome and the position within the LAT promoter whereby an IE3 promoter (ICP4) fragment was inserted upstream of the LAT coding region, thereby replacing a portion of the LAT promoter. The LAT promoter was replaced by the IE3 promoter (ICP4) using the indicated Pst1 sites (P). The location of the 2 kb LAT is shown.

Figure 6A:
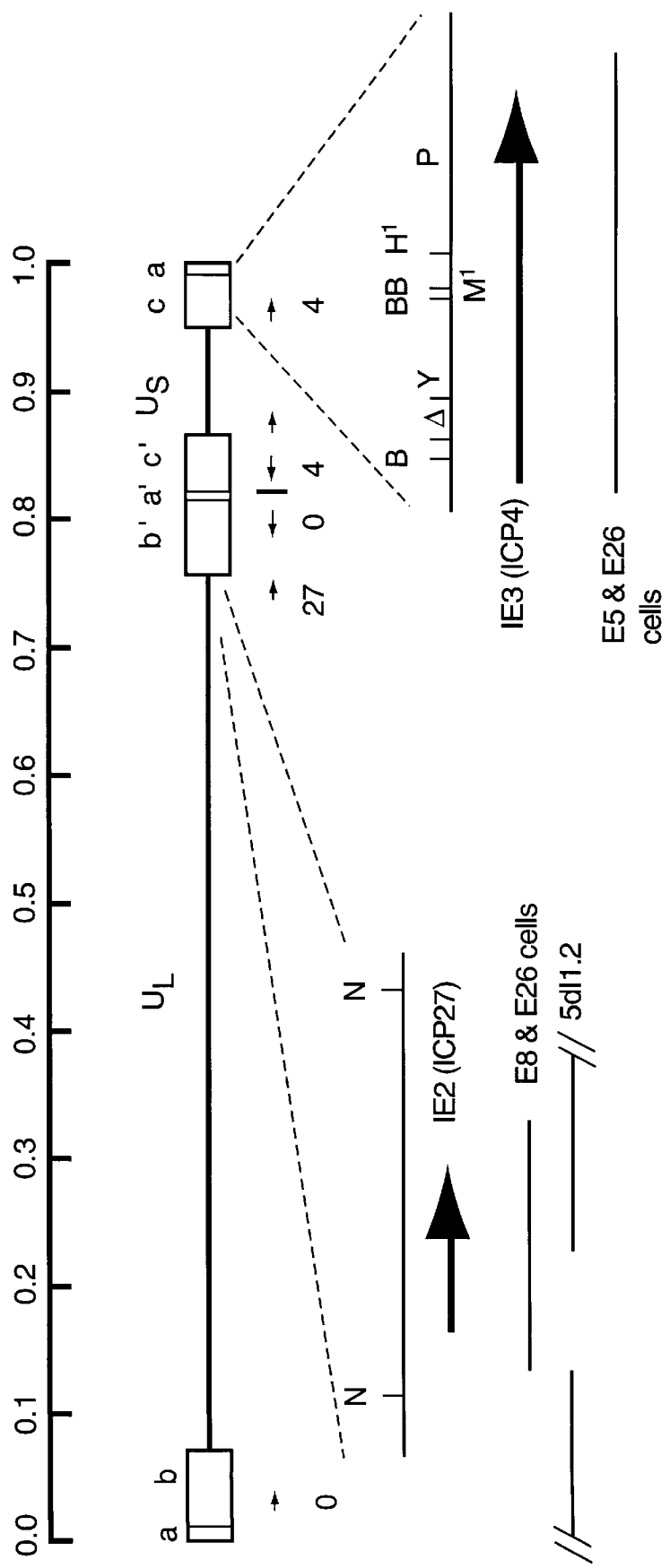
Figure 6B:
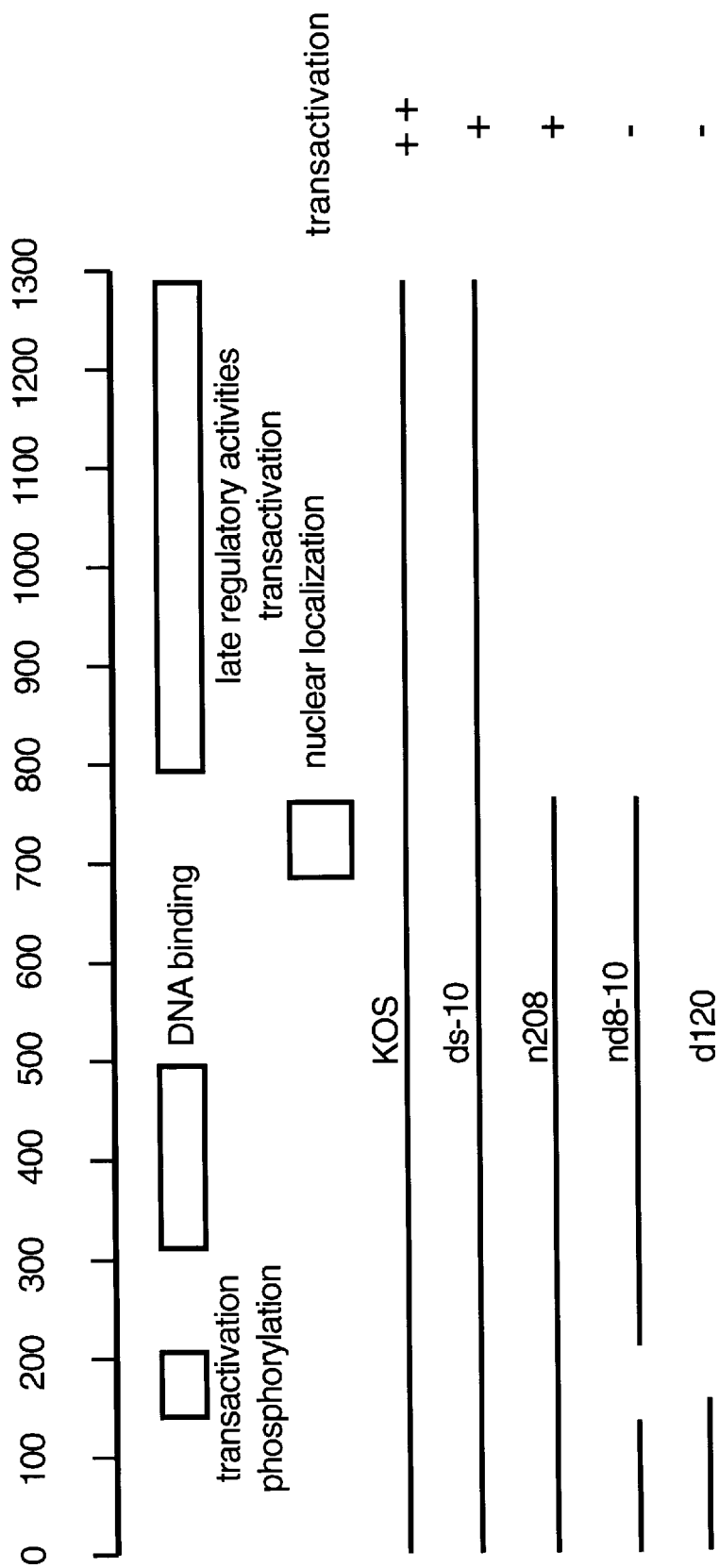

FIG. 6 (Parts A–B) shows structures of viruses carrying deletions in ICP4 and ICP27. (A) The HSV-1 genome is diagrammed showing the unique long ($U_L$) and short ($U_S$) regions and the locations of ICP4 (IE3), ICP27 (IE2) and ICP0 indicated as arrows. The expanded map of ICP4 and ICP27 are shown with the relevant restriction sites: B, BamHI; H, HpaI; N, NruI. BamHI restriction fragments within the ICP4 region include Y, M and P. The short serine-rich transactivation domain deleted in d8-10 and nd8-10 is shown (Δ). The location of the HpaI site specifying translational stop codon in n208 and nd8-10 is indicated as H. The sequences used to generate the ICP4 (E5 and E26) and ICP27-complementing (E8 and E26) cell lines as well the sequence deleted from the ICP27 deletion mutant 5d11.2 are also indicated. (B) The top line represents the 175 Kd ICP4 protein with the number representing amino acids. Important functional domains of the protein are indicated by open rectangles. The coding sequences of mutant ICP4 proteins are shown relative to that of the wild type (strain KOS). The relative transactivation by these proteins is also indicated in the column to the right.

Figure 7:
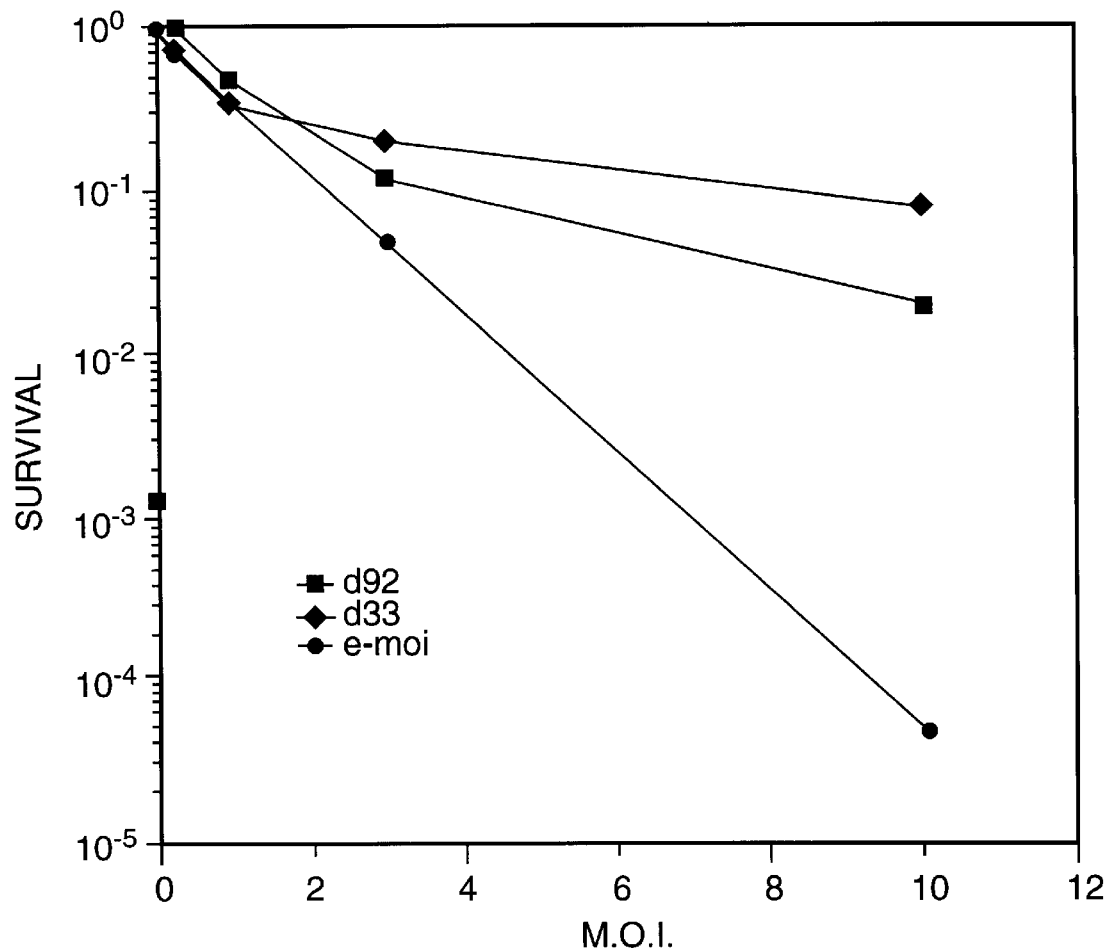

FIG. 7 shows measurements of potential cytotoxicity in d92 and d33. Survival of colony forming ability of Vero cells is plotted as a function of input multiplicity.

Figure 8:
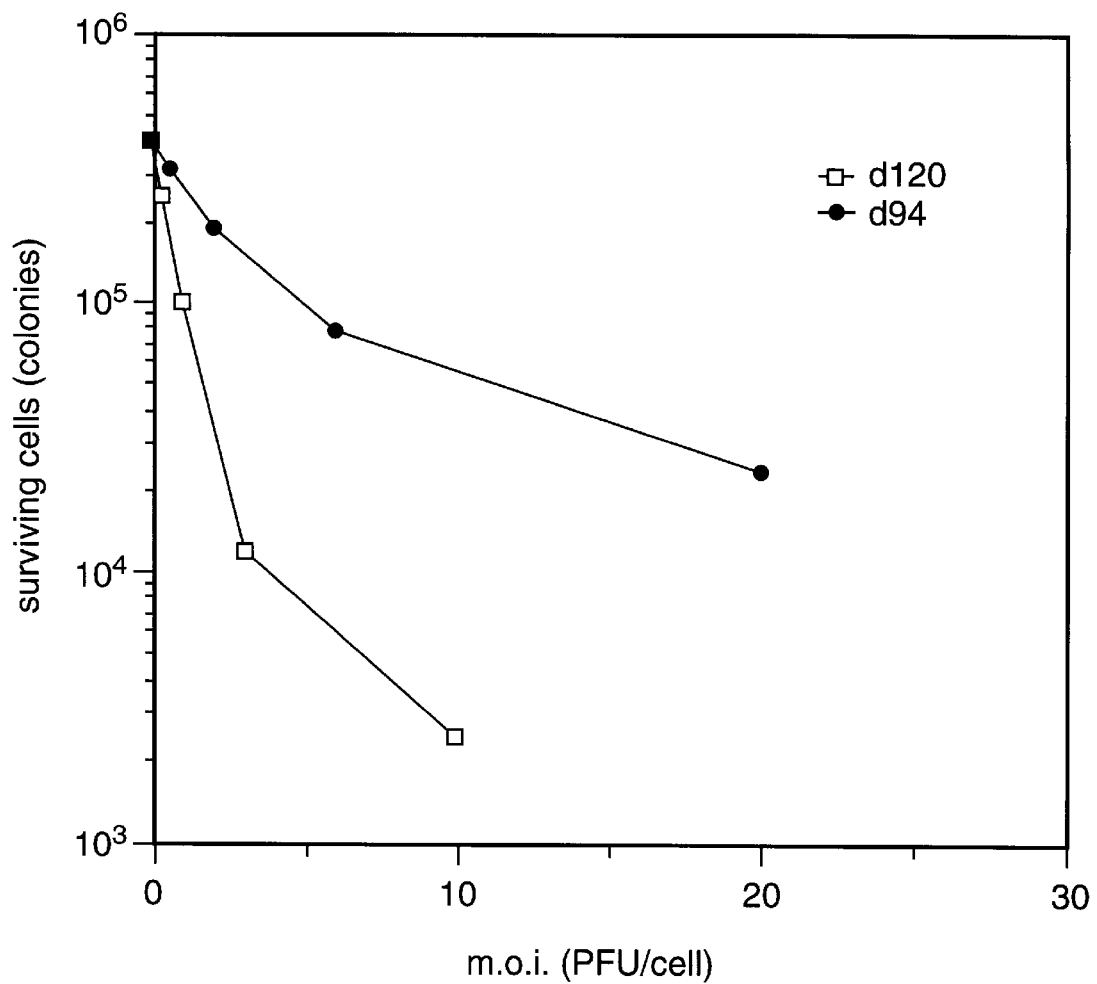

FIG. 8 shows measurements of potential cytotoxicity in d92. As in FIG. 9, survival of colony forming ability of Vero cells is plotted as a function of input multiplicity.

Figure 9:
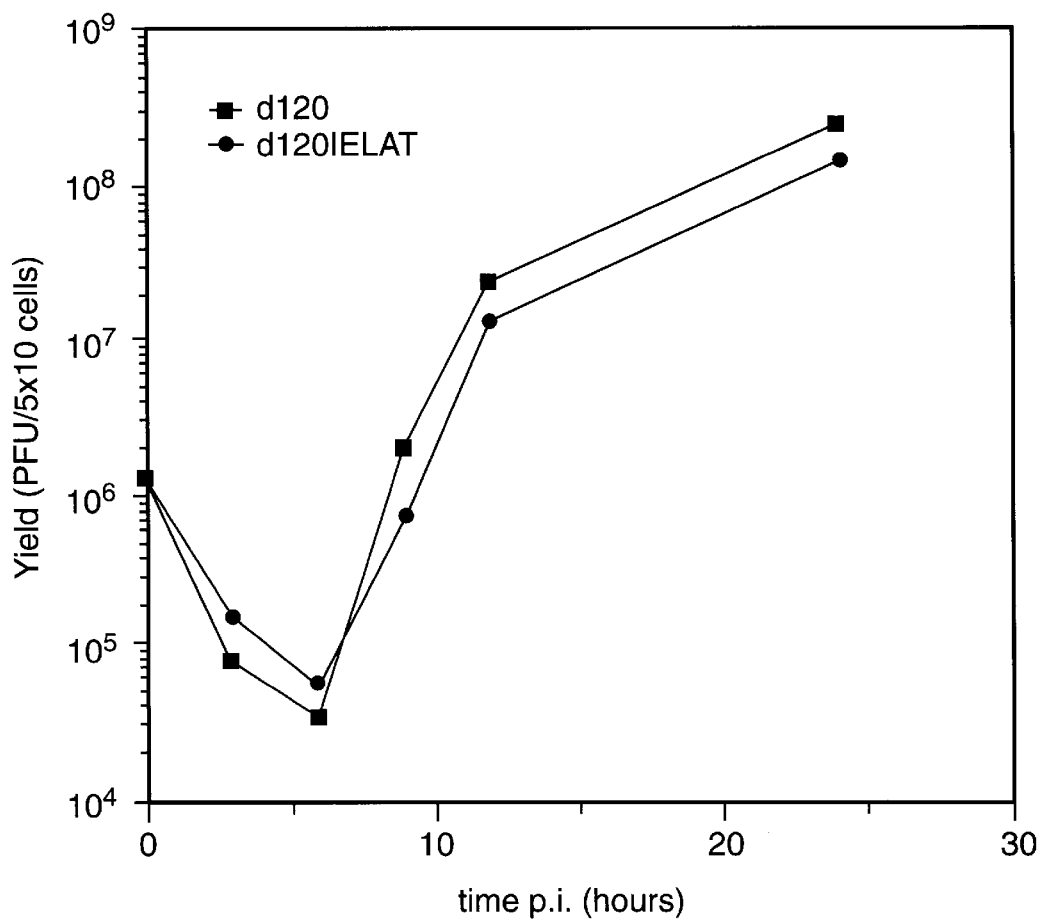

FIG. 9 shows a growth curve of d120 and d120IE3LAT on E5 cells (ICP4$^{(+)}$) as a function of PFU/5×10 cells over 24 hours.

Figure 10:
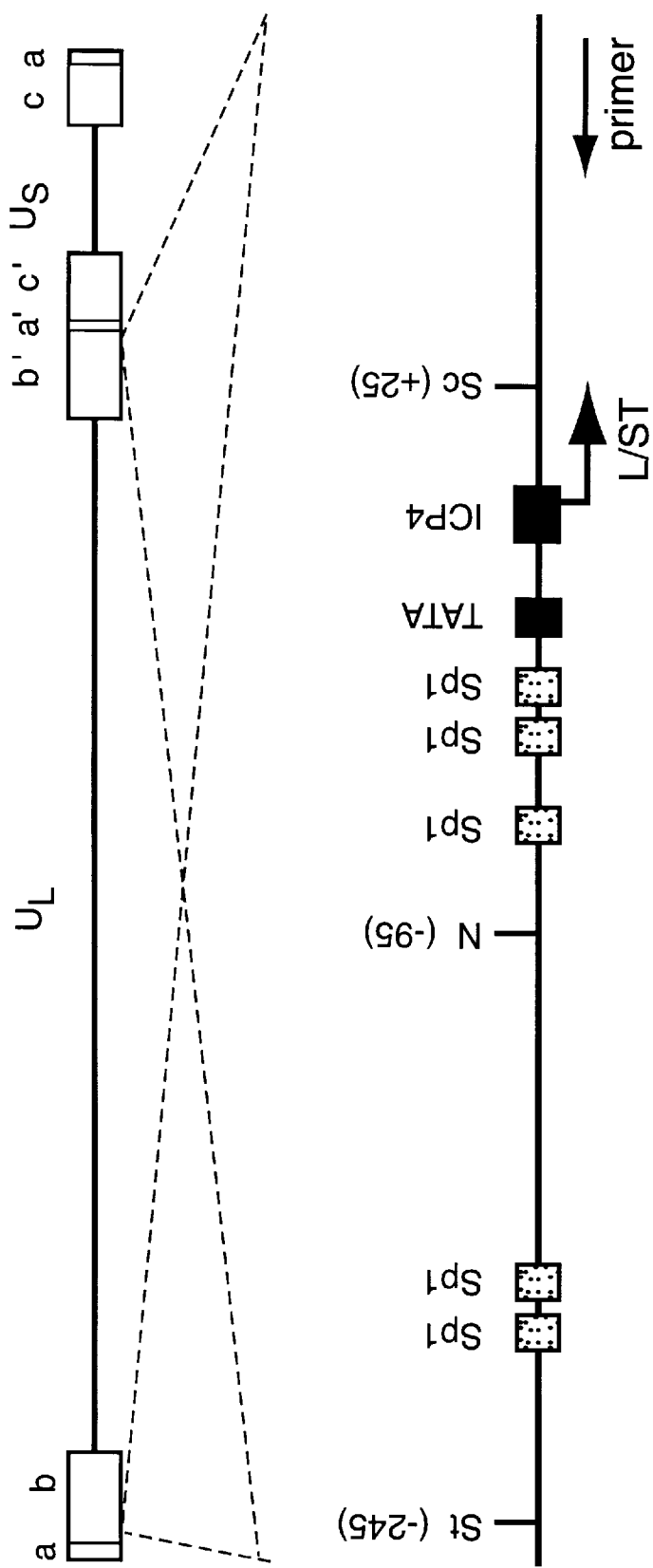

FIG. 10 shows repression of the LS/T promoter in cells infected with viruses defective for ICP4 and ICP27 functions. The genomic location of the LS/T gene is shown spanning the junction between the long and short regions. The transcription control region of the gene is also shown along with the relevant promoter elements including binding sites for Sp1, TBP (TATA box), and ICP4. The restriction sites shown are: N, NotI; Sc, SacI; and St, StuI.

5. DETAILED DESCRIPTION OF THE INVENTION

As used herein, "herpes simplex virus" (HSV) means both type 1 HSV and type 2 HSV.

As used herein, "ICP4$^{(-)}$ICP27$^{(-)}$ HSV strain" means an HSV strain deficient for the HSV genes encoding ICP4 and ICP27.

As used herein, "ICP4$^{(-)}$ICP27$^{(-)}$ additional HSV gene(s)$^-$ HSV strain" means an HSV strain deficient for the HSV genes encoding ICP4, ICP27, and one or more additional HSV genes.

As used herein, "nonessential to HSV gene" means an HSV gene which is nonessential to HSV replication in an ICP4ICP27 complementing cell line.

As used herein, "ICP4$^{(-)}$ICP27$^{(-)}$ nonessential HSV gene(s)$^-$ HSV strain" means an HSV strain deficient for the HSV genes encoding ICP4, ICP27, and one or more nonessential HSV genes.

As used herein, "ICP4$^{(-)}$ICP27$^{(-)}$ additional IE gene(s)$^-$ HSV strain" means an HSV strain deficient for the genes encoding ICP4, ICP27, and one or more additional immediate early HSV genes.

As used herein, "nonessential region" means a region of a genome of an HSV strain where an exogenous gene may be inserted without interfering with virus function.

As used herein, "promoter fragment" means any regulatory region or sequence which functions to effect transcription of a particular DNA fragment from which the promoter fragment is spatially related.

As used herein, "gene product" means any mutated protein fragment, such as, but not limited to a deletion mutation, an addition mutation, a point mutation, or a hybrid peptide, which may or may not exhibit partial or total wild-type biological activity, or a wild-type protein, which is the translation product of a transcribed portion of a respective DNA fragment.

5.1. ICP4$^{(-)}$ICP27$^{(-)}$ HSV Strains and Complementing Cell Lines

The present invention provides for novel cell lines containing DNA encoding for both the HSV proteins ICP27 and ICP4. The present invention also provides a method of producing a cell line containing DNA encoding for both the HSV proteins, ICP4 and ICP27, wherein the method comprises cotransfecting cells capable of hosting HSV with pieces of DNA encoding the HSV protein ICP4, and pieces of DNA encoding the HSV protein ICP27; incubating said cells; and selecting cells harboring both ICP4 and ICP27 encoding pieces of DNA.

The pieces of DNA encoding ICP27 or ICP4 may be introduced into the cell using any DNA delivery system, such as, for example, retroviral vectors, recombinant plasmids, and liposome technology. Cells harboring both ICP4 and ICP27 encoding pieces of DNA may be selected by any available method. For example, the present invention encompasses the method of cotransfecting cells capable of hosting HSV with a piece of DNA encoding the HSV protein ICP4, a piece of DNA encoding the HSV protein ICP27, and a piece of DNA encoding a selection factor; incubating cells; and selecting cells expressing DNA encoding for the selection factor. A selection factor can be anything which will allow for the selection of a cell; such as for example, a neomycin resistance protein.

A novel ICP4ICP27 complementing cell line was produced as follows: plasmids encoding the genes for ICP27 and ICP4 (shown in FIG. 1) were cotransfected with the plasmid pSV2neo into Vero cells and selected with the antibiotic G418. G418 resistant colonies were amplified and tested for the ability to host KOS (wild-type virus), and ICP4$^{(-)}$ virus, d120, and an ICP27$^{(-)}$ virus, 5dl 1.2. All possibilities were obtained: cells that host KOS (all cell lines were able to host KOS), cells that host only d120, cells that host 5dl 1.2, and cells that host both d120 or 5dl 1.2. Curiously, cells that hosted only ICP27$^{(-)}$ virus were far fewer in number than all the other types of cells obtained. Of interest were the cell lines that hosted both d120 and 5dl 1.2. One cell line, designated 26 cells, yielded 900 PFU per cell d120 and 350 PFU per cell 5dl 1.2. Another cell line, designated 8 cells, was retained because it was the only cell line that efficiently hosted 5dl 1.2 and not d120.

Although Vero cells were used in the procedure described hereinabove, it will be appreciated that the present invention encompasses use of any cell line which will host HSV and which will form colonies.

It will be further appreciated that the present invention encompasses use of any delivery system for the pieces of DNA encoding the HSV proteins ICP4 or ICP27 and which will transfect the cell lines utilized. It is preferred that the DNA fragments used to incorporate the ICP4 and ICP27 genes into the cell lines have as few as possible noncoding base pairs on their 3' and 5' ends to limit the generation of wild-type recombinant virus.

Although the plasmid pSV2neo and the antibiotic G418 were used in the procedure described hereinabove, it will be appreciated that the present invention encompasses use of any piece of DNA encoding a selection factor and any accompanying compound or technique that allows for selection of cells hosting the selection factor. It will further be appreciated that the present invention encompasses transfecting only ICP4 and ICP27 encoding pieces of DNA and using any system which allows for selection of cells harboring the ICP4 and ICP27 encoding DNA pieces. It will further be appreciated that the present invention encompasses the use of any means of introducing ICP4$^{(+)}$, ICP27$^{(+)}$ and selection factor genes into cells including but not limited to retroviral vectors, recombinant plasmids, and liposomes.

Although HSV-1 KOS wild-type virus was used in the procedure described hereinabove, it will be appreciated that the present invention encompasses use of any wild-type HSV-1 or HSV-2 virus containing both the ICP4 and ICP27 genes.

Althohugh d120 and 5dl 1.2 were used in the procedure described hereinabove, it will be appreciated that the present invention encompasses use of any ICP4$^{(-)}$ or ICP27$^{(-)}$ HSV strains.

The method of producing a novel ICP4$^{(+)}$ICP27$^{(+)}$ cell line disclosed hereinabove is unique in that those skilled in the art would not have thought it possible to get a significant number of cells accepting both the cotransfected pieces of DNA encoding for ICP4 and pieces of DNA encoding for ICP27 and have those cells express complementing levels of both ICP4 and ICP27. The prior art teaches that such a method would produce almost solely ICP4$^{(+)}$ or ICP27$^{(+)}$ or ICP4$^{(-)}$ICP27$^{(-)}$ cell lines. Furthermore, the prior art teaches that the toxic effects of the two ICP4$^{(+)}$ and ICP27$^{(+)}$ vectors may kill any ICP4$^{(+)}$ICP27$^{(+)}$ cell almost immediately. Despite the need for such cell lines, prior research has taught that such a method would not be efficient enough to produce a cell line hosting both ICP4$^{(+)}$ and ICP27$^{(+)}$ vectors.

Production of the novel ICP4$^{(+)}$ICP27$^{(+)}$ cell lines has allowed the inventor to provide for novel recombinant HSV strains deficient for both ICP4 and ICP27. The present invention provides a method of producing a HSV strain whose genome is deficient for the HSV genes encoding for ICP4 and ICP27, wherein the method comprises coinfecting ICP4ICP27 complementing cells containing DNA encoding for the HSV proteins ICP4 and ICP27 within HSV strain deleted for the ICP4 gene and an HSV strain deleted for the ICP27 gene; incubating the cells; plating virus progeny from the incubated cells on the ICP4ICP27 complementing cells, ICP27 complementing cells, ICP4 complementing cells; and ICP4$^{(-)}$ICP27$^{(-)}$ cells; picking plaques; and identifying virus that plaque on ICP4ICP27 complementing cells and do not plaque on ICP27 complementing cells, ICP4 complementing cells, or ICP4$^{(-)}$ICP27$^{(-)}$ cells.

Novel ICP4$^{(-)}$ICP27$^{(-)}$ HSV strains were produced as follows: 26 cells were coinfected with d120 and 5dl 1.2, plating the progeny on 26 cells, picking plaques, and identifying isolates that plaque on 26 cells and do not plaque on 8 cells (ICP27 complementing), E5 cells (ICP4 complementing), or Vero cells. These corresponded to 8% of the total progeny; a frequency consistent with the distance between ICP4 and ICP27. Individual plaque isolates that only grew on 26 cells were examined by Southern blot hybridization to ascertain the presence of both mutations in cis. One such isolate (d92) was chosen for further study.

A Southern blot comparing the regions of the genome encoding ICP4 and ICP27 from KOS, d120, 5 dl 1.2 and d92 was generated. The probe for ICP27 was the fragment used to generate the 26 cell line. It hybridizes to the indicated Nru I fragment in wild-type virus and in d120, and to a deleted form of the Nru I fragment in 5dl 1.2 and d92. The probe used for ICP4 was also the same used to generate the 26 cell line, except that the ICP4 promoter was not present in the probe. It hybridized to the indicated ICP4 containing fragments, Bam HI K, P, Y and M'. M' runs off the gel because of its small size. d120 and d92 show the characteristic deletion pattern consistent with the documented 4.1 kb deletion. The heterogeneity in the size joint Bam HI fragment is due to variation in the number of "a" sequences in individual genomes. Therefore, d92 contains the intended deletions in ICP4 and ICP27, and behaves functionally as double deletion mutant.

Although Vero cells were used in the procedure described hereinabove, it will be appreciated that the present invention encompasses use of any cell line which will host HSV and which will form colonies.

Although E5 cells and 8 cells were used in the procedure described hereinabove, it will be appreciated that the present invention encompasses the use of any ICP4 complementing cells and any ICP27 complementing cells.

Although d120 and 5dl 1.2 were used in the procedure described hereinabove, it will be appreciated that the present invention encompasses use of any ICP4$^{(-)}$ or ICP27$^{(-)}$ HSV strains.

Figure 1:
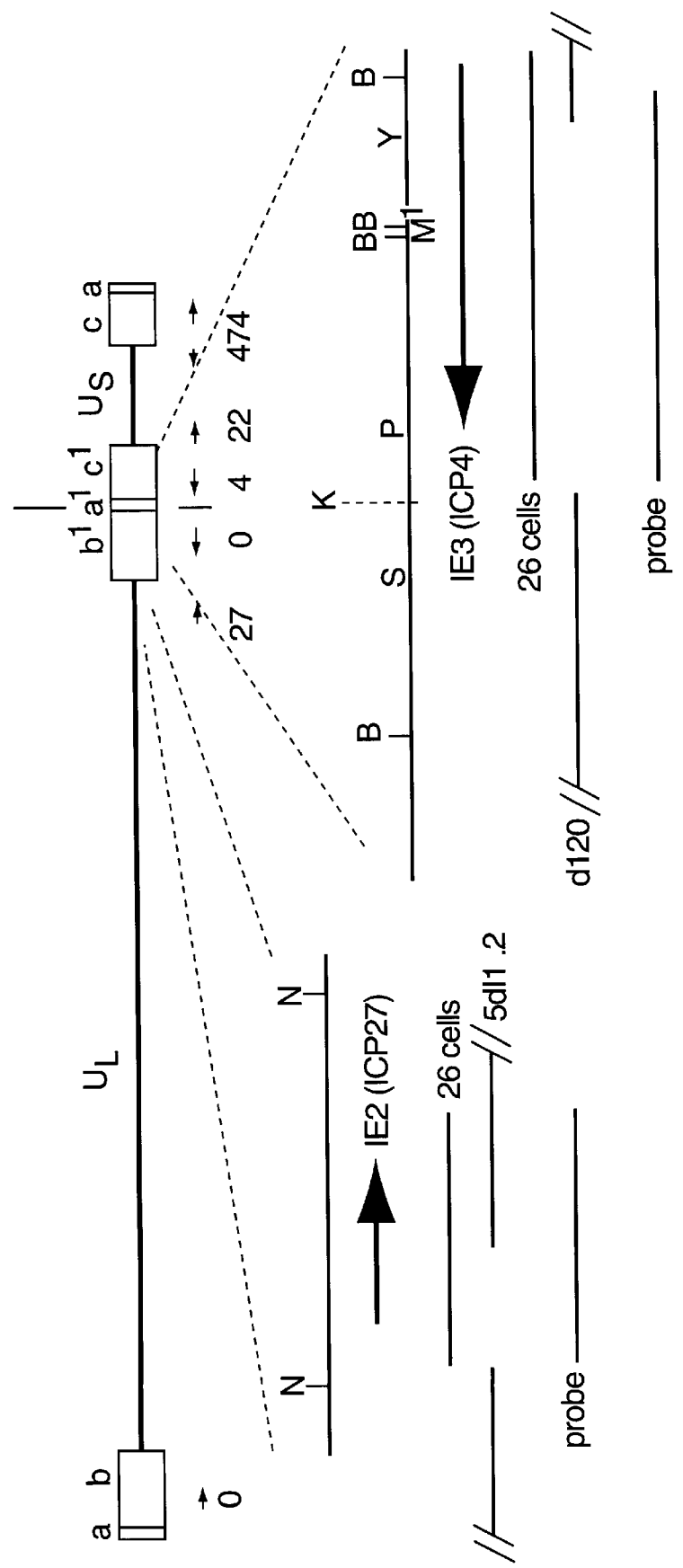
FIG. 1 shows representations of the HSV genome, the genes encoding for ICP27 and ICP4, the 5 dl 1.2 and d120 virus genomes with their ICP27 and ICP4 encoding fragments delineated, ICP27 and ICP4 probes.

It is preferred that the ICP4 or ICP27 deletions in the ICP4$^{(-)}$ and ICP27$^{(-)}$ viruses be as large as possible. As shown in FIG. 1, the deletions in these viruses extend beyond the sequence of the DNA fragments used to incorporate the ICP27 and ICP4 genes in the complementing cell line. Therefore, the copies of these genes resident in the transformed cell line lack the flanking homology necessary to rescue either of the mutations in the double mutant viral genome by homologous recombination.

The present invention provides for methods of efficiently growing the novel ICP4$^-$ ICP27$^{(-)}$ HSV strains disclosed herein. The method comprises infecting 26 cells with the novel ICP4$^{(-)}$ICP27$^{(-)}$ HSV strains, incubating the infected cells, and collecting the progeny virus. Due to the efficiency of these cell lines, the inventor has been able to obtain stock titers of this virus in excess of $10^9$ plaque forming units (PFU) per milliliter. This demonstrates efficient growth in the complementing cells. The prior art teaches that such growth should not be produced.

This efficiency ensures that additional genetic manipulations of the virus that have relatively mild growth damping effects may be performed, such as deletion of the remaining IE genes. The high titers obtainable in this system are also in great excess of those obtained with any of the currently used viral vector systems known to the inventor.

As far as viral vector systems are concerned the ICP4$^{(-)}$ ICP27$^{(-)}$ system described herein is considered a "helper-virus free" system. Most viral vector systems which depend upon helper virus for adequate titers of recombinant virus are notorious for the generation of wild-type, potentially pathogenic revertants. Until now, the best one has been able to do with a herpes virus system is a frequency of wild-type generation somewhat less than $10^{-6}$. Due to its construction, the ICP4$^{(-)}$ICP27$^{(-)}$ system described herein has a theoretical wild-type generation frequency less than $10^{-12}$.

The methods of producing and growing the novel recombinant ICP4$^{(-)}$ICP27$^{(-)}$ HSV strains is novel in that novel ICP4$^{(+)}$ICP27$^{(+)}$ cell lines are utilized.

A a long continuous protein labelling pattern for uninfected (M), KOS, d120, 5 dl 1.2- and d92-infected cells was generated. All viruses show some degree of shut off of host cell protein syntheses. This is probably due to the virion associated shut off gene, vhs. The only discernable viral protein present in the d92 profile is ICP6, the large subunit of ribonucleotide reductase. The absence of ICP0 in this long term label is probably due to an alteration in the stability of ICP0 as a function of the absence of ICP27. ICP0 is made to the same degree in d92 as in d120 in pulse labelling experiments. ICP27 alters the phosphorylation of a variety of proteins, including ICP0. Thus d92 does not express ICP27 or the 175 kd ICP4 protein.

In order to assess the utility of d92 and its potential derivatives as a gene transfer vector, experiments were performed to determine if and for how long d92 genomes can functionally persist in infected cells. The bases for the measurement is the ability to rescue d92 genomes via complementation with an infecting virus that has a mutation in essential gene other than ICP4 or ICP27. This method is illustrated schematically in FIG. 2.

Figure 2:
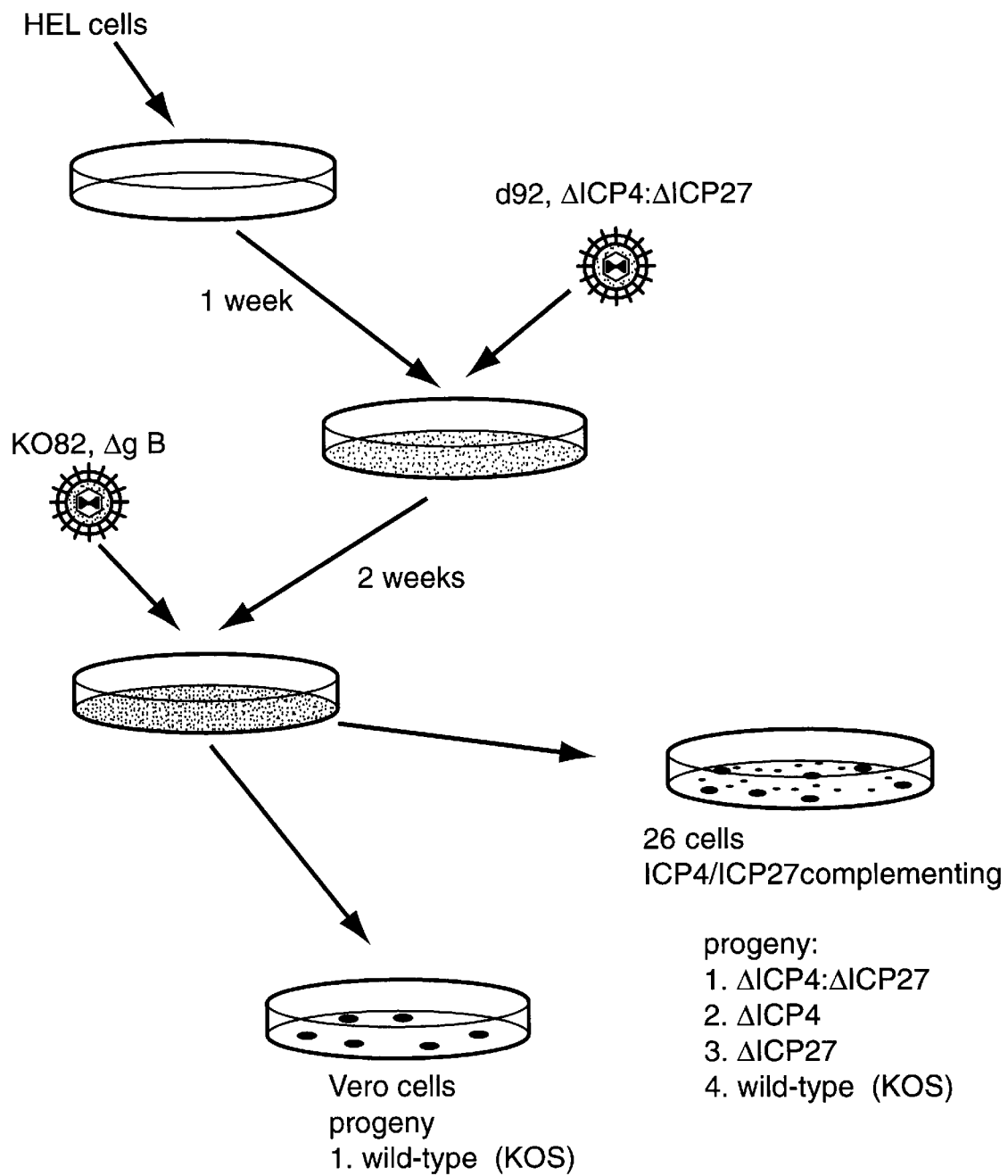
FIG. 2 shows the general method of producing d92-persistently infected HEL cells, the reactivation of virus with HSV K082 and the assay for reactivating virus on 26 cells and Vero cells.

As a direct indication of the usefulness of d92, and any of its derivatives, the following experimental approach was adopted (FIG. 2). One week old confluent normal human (primary) fibroblasts (HEL) cells were infected with d92 at a range of multiplicities of infection from 0.1 to 10 PFU/cell. At 3 and 10 PFU/cell cytopathic effects were seen at 48 hours post-infection that were less pronounced than with d120. All the infected monolayers of HEL cells were completely restored by one week post-infection. At two weeks post-infection, the monolayers were infected with K082 (moi=3PFU/cell), a gB deletion mutant that requires gB transformed cells for growth. 18 hours later, the monolayers were harvested for quantitation of infectious virus.

Figure 3:
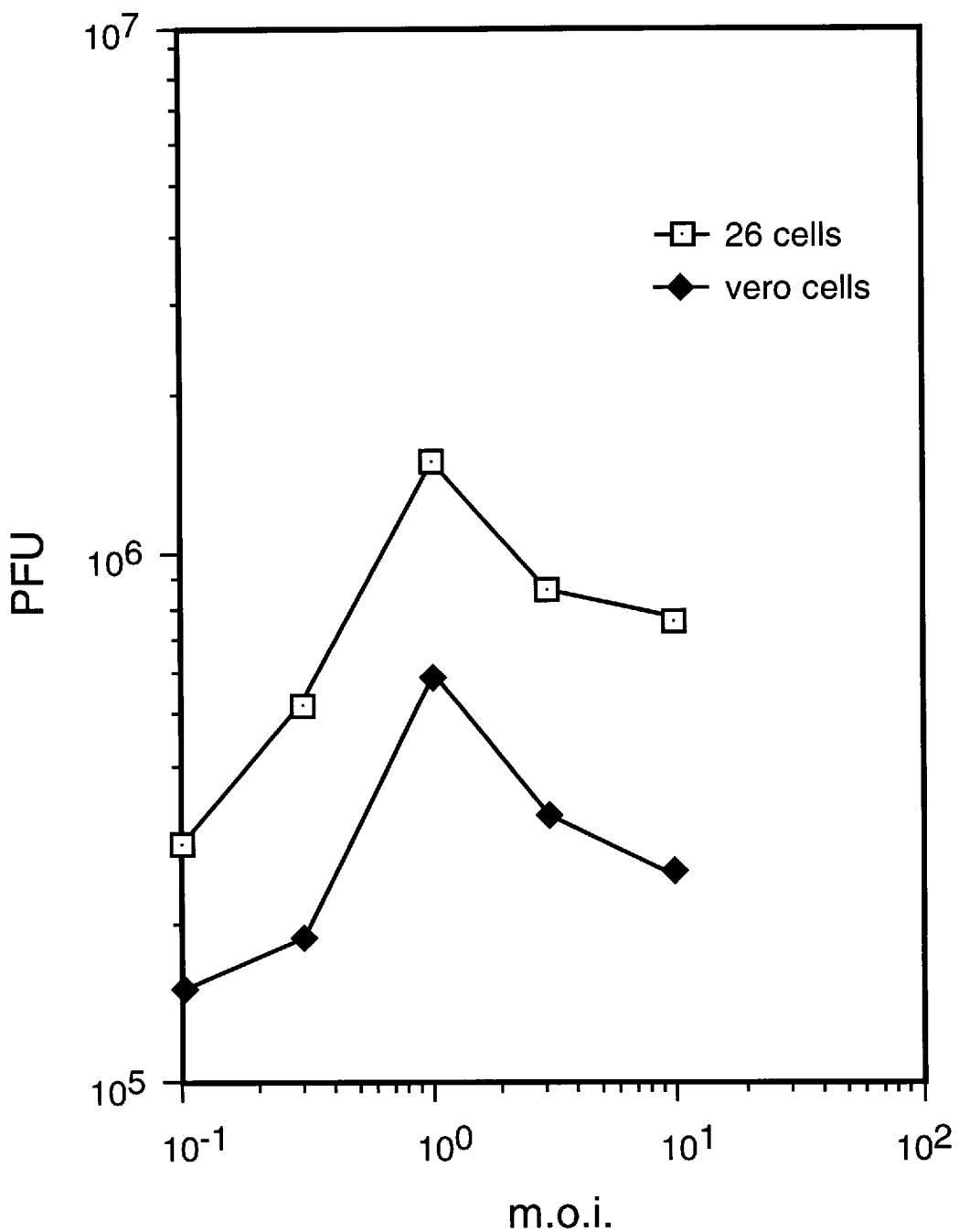
FIG. 3 is a graph of titers of progeny that can be reactivated from human embryonic lung cells persistently infected with d92, which plate on 26 cells and on Vero cells as a function of initial input of d92. 26 cells are an ICP4$^+$ICP27$^+$ cell line.

Shown in FIG. 3 are the titers of progeny that plate on 26 cells and on Vero cells as a function of initial input of d92. Three important observations can be made from the data shown in FIG. 3: (1) Substantial amounts of virus could be obtained from the week old infected cultures at all the multiplicities tested. No virus was obtained from cells infected with d92 at any of the multiplicities if the cells were not infected with K082 (data not shown); (2) The yield of the progeny on 26 cells was three fold higher and the plaques were smaller than that on Vero cell. Southern blots on progeny picked off of 26 cells demonstrated the presence of the deletions in ICP4 and ICP27 in the rescued virus population; and (3) The yield of virus increased linearly up to 1 PFU/cell after which the yield decreased.

From these results it is clear that a substantial number to functional d92 genomes persisted in the infected HEL cells at two weeks post-infection. Moreover, the cells retained viability sufficient to support HSV infection. The appearance of progeny on Vero cells is due to recombination between the persistent d92 genomes and the infecting K082 genomes. This is to be expected given the genomic distance between gB and ICP27. The decline in virus yield for moi's of d92 greater than 1 most probably reflects the residual cytotoxicity of d92.

Figure 4:
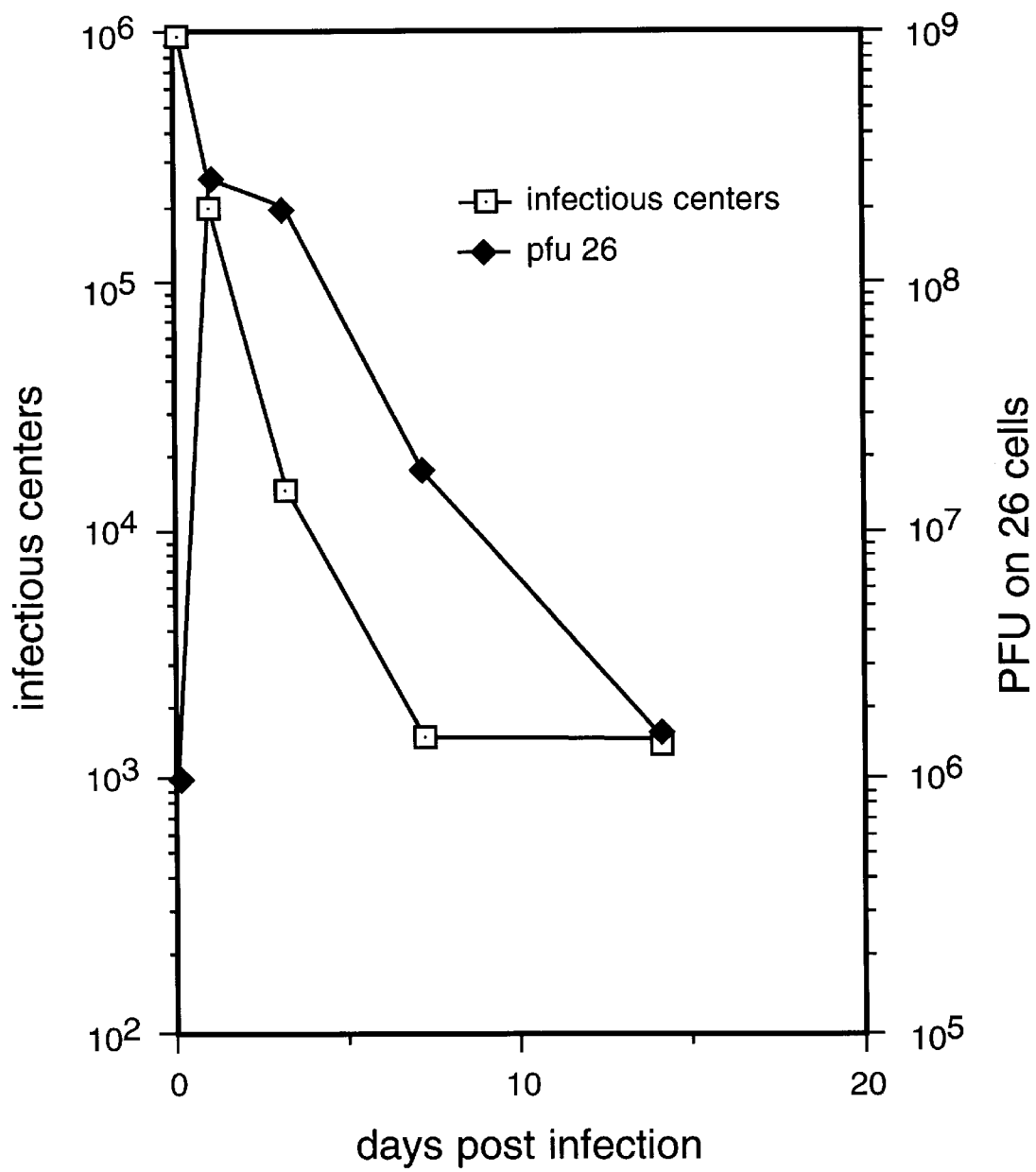
FIG. 4 is a graph of infectious centers and virus yield resulting from reactivation of d92-persistently infected HEL cells measured on 26 cells, as a function of time post-infection.

In the experiment discussed hereinabove it was established that the greatest number of functional d92 genomes persist in the HEL cells when an moi of 1 PFU/cell was used. The following experiment was performed in order to determine the number of functional persistent genomes as a function of time post-infection. Cultures of $10^6$ one week old HEL cells were infected with d92 at an moi of 1 PFU/cell. At 1, 3, 7 and 14 days post-infection the cultures were infected with K082 at an moi of 3 and incubated for 5 hours for infectious centers, or 18 hours for total virus yield. For infectious centers, the monolayers were trypsinized, diluted and plated on 26 and Vero cells. For total virus yield, the monolayers were scraped into the medium, freeze-thawed, and sonnified. The suspension was then clarified by centrifugation, diluted and plated on 26 and Vero cells. As before, the number of plaques on 26 cells was always about 2 to 4 times the number of Vero cells. Shown in FIG. 4 are the infectious centers and virus yield measured on 26 cells, as a function of time post-infection. The infectious center assay was problematic in that it was not possible to obtain single cell suspensions. If the infectious center assay were accurate, then the burst size of d92 at 3 and 7 days would be $10^4$. Wild-type HSV under optimum conditions is $10^3$.

From the burst experiment, an estimate that there is at least $10^4$ functional genomes (to give $2 \times 10^6$ rescued progeny) persisting at two weeks post-infection is obtained. It is not known whether there are more intact genomes in the cells that are not rescued, or whether parts of the 150 kb genome are also present in some cells. Given that ICP27 and ICP4 are the only absolutely essential genes that are expressed during the IE phase of viral gene expression, and that functional IE genes are required for expression of the remainder of the viral genome, it follows that deletion of ICP4 and ICP27 allow for the deletion or inactivation of the remainder of the IE genes, generating a viral genome that is transcriptionally silent in the absence of exogenously added ICP4 or ICP27. The generation of a viral genome that will enter the nucleus and not express any of its encoded genes will eliminate the cytotoxic effects associated with the expression of IE proteins. This will allow for the expression of a foreign gene (under the appropriate promoter control) from the efficiently delivered HSV genome without cytotoxic side effects. This is desirable from the standpoint of safe and efficient gene therapy schemes.

5.2 $ICP4^{(-)}ICP27^{(-)}$ Essential HSV Gene(s)$^-$ HSV Strains

So far, the production of virus (d92) that is deficient for the only two essential IE genes, ICP4 and ICP27 has been described. The expression of viral genes in the d92 background is limited to ICP6, ICP0, ICP22 and ICP47. Although the ICP0 protein is expressed from the d92 genome, its stability may be reduced due to the absence of ICP27 gene product. As previously stated, an important feature of this system is that the flanking homologies necessary to rescue the deletions in the virus (d92) are not present with the genes resident in the complementing cell line (26 cells). Therefore, the generation of wild-type recombinants is an extremely improbable event, and in practice, they are not seen. This is extremely important not only from the standpoints of the development of "safe" vectors but also for the ability to delete other viral genes that may have a growth dampening effect.

The present invention provides for novel HSV strains deficient for ICP4, ICP27, and one or more additional HSV genes, including HSV strains deficient for all IE genes. Some of these HSV strains will be transcriptionally silent in the absence of exogenously added ICP4 and ICP27. The generation of a viral genome that will enter the nucleus and not express any of its encoded genes will eliminate the cytotoxic effects associated with he expression of IE proteins. This will allow for the expression of a foreign gene (under the appropriate promoter control) from the efficiently delivered HSV genome without cytotoxic side effects. This is desirable from the standpoint of safe and efficient gene therapy schemes.

5.3 $ICP4^{(-)}ICP27^{(-)}$ Additional Non-Essential HSV Gene(s)$^-$ HSV Strains As discussed throughout this specification, ICP4 and ICP27 are the only immediate early proteins absolutely essential for virus growth. The basis for the construction of the nontoxic HSV vectors is provided within this specification by the derivation of a system to propagate HSV strains deleted for ICP4 and ICP27. Construction of $ICP4^{(-)}ICP27^{(-)}$ HSV strains as discussed in this specification render possible the deletion of additional HSV genes, resulting in $ICP4^{(-)}ICP27^{(-)}$-based HSV strains with a concomitant decrease in host cell toxicity.

The present invention discloses that infection of an $ICP4^{(-)}ICP27^{(-)}$ HSV mutant in a eukaryotic cell, as exemplified by d92 infection of Vero cells, results in (1) ICP6 being the only discernable immediate-early protein expressed post-infection, and (2) that some degree of shut off of host protein synthesis occurs post-infection.

To this end, the present invention discloses additional recombinant HSV mutant strains derived from d92 or a d92-based genome, any such HSV strain being deficient in ICP4, ICP27 and one or more essential and/or non-essential HSV gene(s).

The HSV recombinant strain d33 $\Delta$(ICP4:ICP27:UL41) is a specific embodiment of the present invention wherein the HSV UL41 gene is mutated in the d92 background. The wild type UL41 gene encodes a 58 kD viral tegument protein involved in the virion-host shutoff (vhs) of protein synthesis. UL41 is a late HSV gene product released during host cell infection. Infection of a eukaryotic cell by wild type HSV is accompanied by early inhibition of host cell metabolism, including DNA and protein synthesis. This viral induced shut-off of host metabolism is linked to destabilization and degradation of host mRNA. Therefore, an $ICP4^{(-)}ICP27^{(-)}$ HSV strain further deficient in UL41 confers additional protection against potential cytotoxic effects by severely reducing viral protein synthesis through the knockout of ICP4 and ICP27 as well as inhibiting viral induced shutoff of host cell metabolism. d33 has been generated by a recombinational cross of d92 with a UL41 deficient-HSV strain in the complementing cell line, 26 cells. This HSV triple mutant strain, d33 $\Delta$(ICP4:ICP27:UL41), is comprised of a genome 11 kb shorter than wild type HSV.

A further embodiment of the present invention discloses an additional novel recombinant HSV strain deficient for ICP4, ICP27, UL41 and the non-essential HSV gene, UL39. In a specific embodiment, presented to exemplify but not limit the claimed invention, d33 was utilized as a template to generate a quadruple HSV mutant deficient in UL39, as well as the ICP4, ICP27 and UL41 mutations within the d33 background. The HSV gene UL39 encodes the large subunit of ribonucleotide reductase, a key enzyme in the pathway reducing ribonucleotides to the corresponding deoxyribonucleotides.

The quadruple HSV mutant strain generated from the d92/d33 mutant HSV series is exemplified in the present invention by d94 $\Delta$(ICP4:ICP27:UL41:UL39):$\beta$-gal. The heterologous $\beta$-gal gene of d94 is abundantly expressed in infected Vero cells without altering cell morphology. Therefore, successful infection of the target cell by d94 results in (1) expression of the gene of interest, (2) an extreme reduction in cytotoxic effects due to viral gene expression, and (3) a persistence of host cell protein synthesis due to inactivation of the UL41 gene product.

Therefore, the present invention discloses HSV mutant strains containing multiple deletions in both essential and non-essential viral genes. These HSV mutant strains, exemplified in this specification by d92, d33 and d94, comprise characteristics amenable to use as gene transfer vehicles, including but not limited to (1) the ability to obtain large quantities of recombinant virus, (2) a significant reduction in wild-type reversion, (3) an ability to accept larger foreign DNA fragments for gene transfer applications, and (4) reduced host cell cytotoxicity.

5.4. Overexpression of LAT From HSV Vector Strains

The present invention discloses additional novel strategies for generating recombinant HSV vectors: these resulting HSV vectors possessing the above-mentioned characteristics as well as promoting latency within the infected target cell. This group of recombinant HSV vectors promote latency within the infected target cell by increasing the concentration of HSV latency-associated transcripts (LATs). LATs are the only viral transcripts that abundantly accumulate during latent infection with HSV in vivo (Spivack and Fraser, 1988, J. Virol 62:3281–3287; Stevens, et al., 1987, Science 235:1056–1059). The HSV genomic location for LATs relative to the IE110 gene (encoding ICP0) is shown in FIG. 5. Multiple promoter regions may contribute to LAT transcription in lytic and latent infection. However, the predominant promoter for LAT transcription is located within a 203 bp PstI fragment comprising −594 to −797 of the LAT upstream region (Batchelor and O'Hare, 1990, J. Virol 64:3269–3297). Deletion of this region greatly reduces LAT accumulation in vivo. I have shown in the course of my research that (1) the late accumulation of LAT, as noted in the art, is due to the binding of the ICP4 protein near the start site of LAT transcription, and (2) LAT is not expressed from viruses deficient for ICP4.

The present invention relates to recombinant HSV strains exhibiting increased expression of LATs, thus promoting latency and a decrease in ICP0 concentration within the target cell.

An embodiment of the present invention discloses an ICP4$^{(-)}$ HSV strain as a template to generate a recombinant HSV vector, this resulting recombinant HSV vector characterized by replacement of an inducible portion of the LAT promoter region with a heterologous promoter fragment that is active in an ICP4$^{(-)}$ HSV genomic background. Such a recombinant HSV vector promotes viral latency while inhibiting the lytic-promoting function of ICP0.

In a further embodiment of the present invention, an ICP4$^{(-)}$ HSV strain is utilized as a template to generate a recombinant HSV vector, this resulting recombinant HSV vector characterized by removal of a region of the LAT promoter from about −594 bp to about −797 bp and replacement with a heterologous promoter fragment such that LAT will be expressed in the ICP4$^{(-)}$ background of this recombinant HSV vector.

In a specific embodiment of the present invention, an ICP4$^{(-)}$ HSV recombinant vector is used as a template to generate a HSV recombinant vector, this resulting recombinant HSV vector characterized by replacement of a portion of the LAT promoter region with the IE3LAT construction, depicted in FIG. 5 and described in detail in the Example section.

In a preferred embodiment of the present invention, the recombinant HSV vector is d120IE3LAT. The mutant HSV strain d120IE3LAT, in contrast to d120, shows a marked increase in LAT expression and a significant decrease in ICP0 expression.

The premise of these HSV recombinant constructions is expression of adequate levels of LAT in a HSV background devoid of such expression in order to promote latency within the infected target cell. ICP4$^{(-)}$ strains do not activate expression of LAT from the wild type LAT promoter region. ICP4$^{(-)}$ HSV strains result in an increase in ICP0 within the infected cell. Data disclosed within this specification indicates that ICP0 concentration decreases in the presence of LAT expression. Therefore, it is a preferred embodiment of the present invention to introduce an LAT expression cassette in an any ICP4$^{(-)}$ background in order to prevent potential cytotoxic effects of ICP0 within the infected target cell.

By way of example, and not of limitation, the double mutant d92, or a similar ICP4$^{(-)}$ICP27$^{(-)}$ strain, may be utilized as such a starting template. The data disclosed within this specification show that such a recombinant HSV strain would show similar results as reported for d120IE3LAT, plus the additional knockout of the IE2 gene (ICP27 protein).

By way of additional example, and not of limitation, the triple mutant d33 or a similar $\Delta$(ICP4:ICP27:UL41) strain may be utilized as such a starting template. The data disclosed within this specification show that such a recombinant HSV strain should show similar results as reported for d120IE3LAT, plus the additional knockout of the IE63 gene (ICP27 protein) and the UL41 gene (58 kd vhs protein).

It will be evident to one of skill in the art upon review of this specification that any heterologous promoter fragment active in the HSV strain chosen as a template template may be utilized to generate a HSV strain expressing LAT.

5.5 HSV Mutant Strains Expressing Partial Viral Peptides With Altered Biological Activity The present invention also discloses the construction and use of ICP27$^{(-)}$ strains containing an additional HSV genomic deletion encoding a partial ICP4 peptide with anomalous biological activity in relation to wild type ICP4 function(s). It is disclosed within this specification that two of the five HSV immediate early gene products, ICP4 and ICP27, effect viral gene expression and are absolutely essential for virus replication. Data presented within this specification establish functional interactions between ICP4 and ICP27 that contribute to establishing the program of viral gene expression that ensues during lytic infection.

Therefore, the present invention provides for additional HSV viral mutants, mutants simultaneously deleted for the entire ICP27 coding region and defined functional domains of ICP4. These data presented in Example Section 12 demonstrate a clear involvement for ICP27 in the induction of early genes, in additional to its known role in enhancing late gene expression during viral infection. In the absence of both ICP4 and ICP27, viral early gene expression, as measured by the accumulation of tk and ICP6 messages was drastically reduced relative to the amounts of these messages seen in the sole absence of ICP4. Therefore, elevated levels of early gene expression as a consequence of ICP27 occurred in the absence of any ICP4 activity. Evidence is also presented regarding the modulation of the ICP4 repression function by ICP27. When synthesized in the absence of ICP27, a mutant ICP4 protein was impaired in its ability to repress transcription from the LS/T promoter in the context of viral infection and in vitro. The defect correlated with the loss of the ability of this mutant protein to bind to its recognition sequence when produced in infected cells in the absence of ICP27. These observations indicate that ICP27 can regulate the activity of at least one domain of the ICP4 protein as well as contribute to elevated early gene expression independent of ICP4. These data provide additional support for the central theme of the present invention: the utilization of novel ICP4$^{(-)}$/ICP27$^{(-)}$ HSV mutant genomes for use as vectors in various gene therapy applications.

A particular embodiment of the present invention is an ICP27$^{(-)}$:ICP4 partial peptide mutant containing a deletion of the 3' portion of the ICP4 coding region, from about 800 bp to about 1300 bp of the ICP4 coding region, this region encompassing an ICP4 3' transactivation domain.

A ICP27$^{(-)}$:ICP4 3' transactivation domain partial peptide deletion mutant of the present invention is exemplified, but not limited to, the ICP27$^{(-)}$:ICP4 3' transactivation domain mutant, n208:Δ27.

Another specific embodiment of the present invention is an ICP27$^{(-)}$:ICP4 partial peptide mutant containing two deletions: a deletion of the 3' portion of the ICP4 coding region, from about 800 bp to about 1300 bp of the ICP4 coding region, and a deletion in the 5' portion of the ICP4 coding region, from about 135 bp to about 200 bp of the ICP4 coding region, this region encompassing an ICP4 5' transactivation domain.

A ICP27$^{(-)}$:ICP4 5'/3' transactivation domain partial peptide deletion mutant of the present invention is exemplified, but not limited to, nd8-10:27.

5.6. Generation of ICP4(-)ICP27(-) Non-Essential HSV Gene(S)$^-$ HSV Strains The present invention provides methods of generating ICP4$^{(-)}$ICP27$^{(-)}$ nonessential HSV gene(s)$^-$ HSV strains. One method comprises coinfection of the ICP4ICP27 complementing cell line with the ICP4$^{(-)}$ICP27$^{(-)}$ HSV strain and an HSV strain harboring a deletion in the desired nonessential gene. At some frequency homologous recombination will generate a ICP4$^{(-)}$ICP27$^{(-)}$ nonessential gene(s)$^-$recombinant virus. The progeny of this coinfection is then plated on ICP4ICP27 complementing cells and ICP4$^{(-)}$ICP27$^{(-)}$ nonessential gene(s)$^-$ HSV strains are selected. Since there is no genetic selection for the ICP4$^{(-)}$ICP27$^{(-)}$ nonessential gene$^-$ virus, Southern blot analysis of individual progeny isolates may be utilized to select ICP4$^{(-)}$ICP27$^{(-)}$ nonessential gene(s)$^-$ HSV strain. The method may be performed again to produce further nonessential gene deletions using the new ICP4$^{(-)}$ICP27$^{(-)}$ nonessential gene(s)$^-$ HSV strain and an HSV strain harboring a deletion in another desired nonessential gene. The method is repeated further as needed to provide an HSV strain having all the desired nonessential gene deletions.

A second method comprises cotransfection of the ICP4ICP27 complementing cell line with the ICP4$^{(-)}$ICP27$^{(-)}$ HSV strain and pieces of DNA encoding for an inactivating mutation of the desired nonessential HSV gene. The pieces of DNA encoding for the inactivating mutation of the desired nonessential HSV gene may be contained within, for example, a plasmid, vector, HSV strain or other delivery vehicle. At some frequency homologous recombination will generate a ICP4$^{(-)}$ICP27$^{(-)}$ nonessential gene(s)$^-$ recombinant virus. The progeny of this cotransfection is then plated on ICP4ICP27 complementing cells and ICP4$^{(-)}$ICP27$^{(-)}$ nonessential gene(s)$^-$ HSV strains are selected. Since there is no genetic selection for the ICP4$^{(-)}$ICP27$^{(-)}$ nonessential gene(s)$^-$virus, Southern blot analysis of individual progeny isolates may be utilized to select ICP4$^{(-)}$ICP27$^{(-)}$ nonessential gene(s)$^-$ HSV strain. The method may be performed again to produce further nonessential gene inactivations using the new ICP4$^{(-)}$ICP27$^{(-)}$ nonessential gene(s)$^-$ HSV strain and pieces of DNA encoding an activating mutation of a further nonessential HSV gene. The method is repeated further as needed to provide an HSV strain having all the desired gene inactivations.

It will be appreciated that the methods of generating ICP4$^{(-)}$ICP27$^{(-)}$ nonessential HSV gene(s)$^-$ HSV strains disclosed hereinabove may be used together.

The present invention encompasses any ICP4$^{(-)}$ICP27$^{(-)}$ one or more additional HSV genes$^-$ HSV strains. Multiple additional HSV genes will be deleted or inactivated one gene at a time. It will be further appreciated that the present invention provides for novel HSV strains that are transcriptionally silent.

Many of the genes within the HSV genome are nonessential to virus reproduction. The present invention provides for novel ICP4$^{(-)}$ICP27$^{(-)}$ nonessential HSV gene(s)$^-$ HSV strains. The present invention provides for methods of efficiently growing novel HSV strains deficient of ICP4, ICP27, and one or more nonessential HSV genes using the novel ICP4$^{(+)}$ICP27$^{(+)}$ cell lines disclosed herein. The method is the same as that used to efficiently grow d92 and comprises infecting 26 cells with the novel ICP4$^{(-)}$ICP27$^{(-)}$ nonessential HSV gene(s)$^-$ HSV strains, incubating the infected cells, and collection the progeny virus. It will be appreciated that this method may be used to grow ICP4$^-$ ICP27$^-$ additional IE-gene(s)$^-$ HSV strains. The herpes virus needs no other IE gene coding proteins besides ICP4 and ICP27 to reproduce. Therefore, the 26 cell line will grow the additionally IE-gene-depleted virus.

As stated hereinbefore, the herpes virus has many properties which would be potentially useful for gene transfer purposes. The present invention provides for novel vectors comprising a novel HSV strain disclosed herein and at least one exogenous gene to be transferred to a cell and appropriate promoter sequences, wherein the gene to be transferred to a cell and the corresponding promoter sequence are contained within one or more nonessential regions of the genome of the novel HSV strains. The nonessential regions of HSV genome are well known to those skilled in the art. The present invention also provides a method of using ICP4$^{(-)}$ICP27$^{(-)}$ HSV strains as vectors, wherein the method comprises inserting at least one exogenous gene and appropriate promoter sequence into the genomes of the ICP4$^{(-)}$ ICP27$^{(-)}$ HSV strains, and then infecting cells with the ICP4$^{(-)}$ICP27$^{(-)}$ HSV strain. The present invention also provides a method of using ICP4$^{(-)}$ICP27$^{(-)}$ additional HSV gene(s)$^-$ HSV strains as vectors, wherein the method comprises inserting at least one exogenous gene and appropriate promoter sequence into the genomes of the ICP4$^{(-)}$ICP27$^{(-)}$ additional HSV gene(s)$^-$ HSV strain, and then infecting a cell with the ICP4$^{(-)}$ICP27$^{(-)}$ HSV gene(s)$^-$ HSV strain.

The inventor has demonstrated that $10^4$ to $10^5$ functional d92 viral genomes persisting in $10^6$ HEL cells at one to two weeks post-infection. This gives a lower limit on the amount to vector delivered DNA persisting in the cells at these times. This efficiency is bound to increase with further HSV gene deletions, which reduce the cytotoxicity of d92. Given the occurrence of a substantial number of persisting genomes, it follows that integration events through nonhomologous recombination will occur between the persisting viral genome and the cellular DNA. Several observations support the occurrence of extremely efficient gene transfer: (1) DNA introduced into mammalian cells is often integrated in nonhomologous sites, (2) Ultraviolet (UV) inactivated HSV were the first virus vehicles used to transform tk$^{(-)}$ cells to the tk$^{(+)}$ phenotype. UV irradiated virus were able to transform cells at low frequencies. For this purpose, high doses of UV are required to inactivate virus stocks to the level that residual infectivity is not a problem. Under these circumstances, the transforming DNA is certain to have incurred significant UV damage; an undesirable property when one wishes to introduce biologically active genetic information. The use of nonirradiated, noncytotoxic vectors would obviate this problem; and (3) This has recently been accomplished for ICP4$^{(-)}$ virus transforming cells with the neomycin resistance gene.

While the ICP4$^{(-)}$ viruses have been shown capable of introducing transforming DNA into cultured cells, several observations suggest that d92 and additional HSV gene deficient viruses will be more efficient: (a) The level of recombinant in the ICP4$^{(-)}$ICP27$^{(-)}$ system are far lower than the lowest obtainable in the ICP4$^-$ system. This will allow us to routinely use higher moi's without the fear of the presence of chance wild-type recombinant; (b) More persistent genomes are obtainable with d92 than ICP4$^{(-)}$ viruses; and (c) Further mutational alterations made on d92 that reduce its cytotoxicity will also increase its transformation efficiency.

The present invention provides that vectors may be produced from the novel HSV strains disclosed herein by any known techniques, including, but not limited to, classical genetic or recombinant techniques. In addition, the novel vectors may be utilized by known methods. For example, a vector for neomycin resistance may be produced and utilized. The gene encoding the bacterial protein neomycin phosphotransferase is contained on the plasmid pSV2neo under the control of the SV40 promoter. The entire gene with the promoter will be placed in the Sac 1 site within the cloned HSV tk gene. The resulting plasmid will be cotransfected with recipient intact viral DNA on complementing 26 cells. The progeny of the transfection will be plated on 26 cells in the presence of acycloguanosine ($1\times10^{-4}$M) for the selection of the tk$^{(-)}$ phenotype. Southern blots on small cultures from individual plaque isolates will be performed to identify the introduced neo$^r$ gene. The desired viruses will be further plaque purified and stocks will be prepared on 26 cells. Vero cells will be used as recipients for the nec$^r$ virus. The stable presence and function of the gene in transformed cells will be selected for by incubation in the drug G418.

As another example, a vector for the human HPRT gene may be produced and utilized. The human HPRT gene under the control of the HSV tk promoter has been cloned into the tk gene of wild-type HSV. This virus is referred to as HSV-HP40 and d92 (or its derivatives) will be coinfected on 26 cells in a classical cross experiment. Progeny that grow in the presence of acycloguanosine (tk interrupted by HPRT) on 26 cells, but not on Vero cells (containing the mutations in ICP4 and ICP27) will be isolated and the genomes examined by Southern blot hybridization to confirm the presence of all the alleles. The distance between ICP27 and tk is great enough to allow 20%–30% recombination. B103-4C cells are a HPRT derivative of B103 rat neuroma cells. Infected B103-4C cells will be incubated in HAT medium to select for HPRT$^+$ transformants. HAT medium contains 110 mM hypoxanthine, 2.3 mM aminopterin, and 20 mM thymidine. The same mechanical procedures will be used for the cloning and DNA analysis of B103-4C cells as were used for Vero cells above.

It will be appreciated that the present invention encompasses use of the novel HSV strains disclosed herein as vectors carrying any genes whose size permits them to be inserted in the HSV genome. It will be further appreciated that the novel vectors disclosed herein may be utilized for gene therapy and other known vector uses.

The HSV mutant strains of the present invention, as exemplified by d92, d33, d94, d120IE3LAT and n208:5 dl 1.2, comprise various characteristics, disclosed within this specification to be used along or in combination, that render these HSV strains as amenable to use as gene transfer vehicles. Such uses include, but are by no means limited to, (1) in vivo delivery of human therapeutic or prophylactic genes of interest to various cell types, (2) in vitro delivery of genes of interest to various cell types, human and/or non-human, (3) use to construct vectors for generation of transgenic mice strains, and (4) use to construct vectors to knockout specific genes in mice strains.

6. EXAMPLE

Construction of 26 Cells

The plasmid pSV2neo contains the gene encoding neomycin phosphoryl transferase and confers resistance to G418 to mammalian cells. The plasmid pK1-2 contains the coding sequence and transcriptional regulatory elements for the expression of ICP4 (DeLuca, et al., 1987, Nucleic Acids Res. 15:4491–4511). It contains approximately 400 bp of HSV-1 sequences beyond the 3' end of the mRNA. The plasmid pKHX-BH contains all the coding sequence of HSV necessary to express ICP27 (Bond, et al, 1984, Virology, 132:368–376). pSV2neo (1 microgram), pK1-2 (3 micrograms), and pKHX-BH (3 micrograms) were cotransfected using the calcium phosphate precipitation method onto $4\times10^6$ ATCC CCL81 Vero cells. Four hours after the application of the precipitate to the cells, they were subjected to a 15% glycerol shock for a period of 2 mins. After the shock, the cells were incubated in DME plus 10% FBS at 37° C. 24 hours later, the cells were trypsinized and replated at one tenth the original density and G418 was applied (1 mg/ml). After four days, the concentration of G418 was lowered to 400 micrograms per ml. After two weeks, G418 resistant colonies were observed. These were isolated and expanded. Monolayer cultures from individual clones were infected with d120, to determine the functional presence of the ICP4 gene, and 5dl 1.2, to determine the functional presence of the ICP27 gene.

Of the 67 cell lines tested with d120 and 5dl 1.2, 12 allowed the growth of only d120, 4 allowed the growth of only 5dl 1.2 and, 19 of the lines allowed the growth of both. With many of the lines that allowed the growth of both, virus yield experiments were performed to determine the best cell line to use as an efficient host for both mutant viruses. The plaque of d120 and 5dl 1.2 were closest in size to wild-type virus on a cell line designated 26 cells. The yields of d120 and 5dl 1.2 were 810 and 310 PFU/cell, respectively on 26 cells. A cell line designated 8 cells were also retained because they only allowed the efficient growth of 5dl 1.2.

7. EXAMPLE

Construction of d92, an ICP4 and ICP27 Deletion Mutant d120 and 5dl 1.2 were used to coinfect 26 cells at an moi of 5 PFU each. 18 hours later the culture was harvested and the progeny were plated out on 26 cells for the isolation of individual plaques. After the plaques developed, they were picked with a pipet into 0.5 ml medium, freeze-thawed three times and plated on 26 cells (ICP4 and ICP27 complementing), E5 cells (ICP4 complementing), 8 cells (ICP 27 complementing), the Vero cells (noncomplementing). 120 plaque isolates were tested. 29 (24%) of the progeny grew only on E5 cells and 26 cells; these are the ICP4 mutant parent. 63 (53%) grew only on 8 cells and 26 cells; these are the ICP27 mutant parent. 18

(15%) grew on all the cell types; these are wild-type virus recombinant generated by the cross over of DNA from d120 and 5dl 1.2. 10 (8.3%) only grew on 26 cells; these are the ICP27$^{(-)}$ICP4$^{(-)}$ double mutant. These were checked by Southern blot analysis for the presence of the deletion characteristic of both d120 and 5dl 1.2.

It will be appreciated that the present invention discloses novel ICP4$^{(+)}$ICP27$^{(+)}$ cell lines; a method of producing ICP4$^{(+)}$ICP27$^{(+)}$ cell lines; novel ICP27$^{(-)}$ICP4$^{(-)}$ HSV strains, their generation, and use as vectors; ICP27$^{(-)}$ICP4$^{(-)}$ additional HSV gene(s)$^-$ HSV strains, their generation, and use as vectors; novel vectors comprising the novel HSV strains disclosed herein whose genome contains at least one exogenous gene and an appropriate promoter sequence; methods of using the novel HSV strains disclosed herein as vectors; and methods of using the novel HSV disclosed herein to direct homologous recombination with cellular DNA.

8. EXAMPLE

Construction of d33 Δ(ICP4:ICP27:UL41)

ΔSma contains an internal deletion within the UL41 coding region that results in expression of a truncated protein which is not incorporated into virions (Read, et al., 1993, J. Virol. 67:7149–7160). The progeny from a recombinational cross between d92 and ΔSma were plated plated on 26 cells and plaques were chosen for Southern blot analysis. Isolates were selected on the basis of having deletions in ICP4, ICP27 and Ul41. d33 is one such isolate.

A long continuous protein labeling pattern for uninfected Vero cells, wild type HSV (KOS), d120 (ICP4$^{(-)}$), 5dl 1.2 (ICP27$^{(-)}$), ΔSma (UL41$^{(-)}$), and d33 Δ(ICP4:ICP27:UL41), d92 Δ(ICP$_4$:ICP$_{27}$) was generated. All viruses except ΔSma and d33 show some degree of shut off of host cell protein synthesis. This can be attributed to the lack of a stable vhs activity from these UL41$^{(-)}$ strains. Late genes are not expressed in 5dl 1.2 infected cells and only ICP0, ICP6 and ICP27 are expressed in d120 infected cells. Viral gene expression is severely impaired in the d92 background. The only discernable viral proteins present in the d92 profile are ICP6 and ICP0.

The data show further that when UL41 is mutated in the d92 background (i.e., d33), the observed protein expression profile is similar to that seen in uninfected cells. Despite the dramatic restriction in viral gene expression observed for d33 and d92 in noncomplementing cells, wild-type levels of viral gene expression are observed in the complementing cell line, 26 cells. These viruses can be obtained in quantities discussed within this specification (i.e., titers in excess of $10^9$ PFU/ml). Therefore, this specification discloses the generation of large quantities of these mutant HSV vectors that do not have any wild-type recombinants, and upon infection of cells, the pattern of protein synthesis resembles that seen in uninfected cells.

The expected decrease in cytotoxic effects subsequent to target cell infection by d92 and d33 are shown in FIG. 7. The survival of Vero cells infected with d92 and d33 is reported as a function of multiplicity of infection (m.o.i.). Vero cells are a standard cell line used for the propagation of HSV and are the cells most sensitive to cytotoxic effects of defective HSV mutants (Johnson, et al., 1992, J. Virol. 66:2952–2965). Therefore, Vero cells represent a rigorous test of cytotoxic potential. Monolayers of Vero cells were infected at the indicated m.o.i.s, incubated for 6 hours and then trypsinized, diluted, and plated out for colonies. At 10–14 days post infection the number of colonies were quantified and are represented as a ratio to the number obtained for uninfected cells. The survival curves demonstrate that even when cells are multiply infected with d33, greater than 20% of the infected cells survive the infection and can go on to form colonies. Also shown is the anticipated survival if every infection resulted in cell death ($e^{-m.o.i.}$). The survival of both these viruses is markedly increased over an ICP4$^{(-)}$ recombinant virus such as d120.

9. EXAMPLE

Construction of d94 Δ(ICP4:ICP27:UL41:UL39):β-GAL

The plasmid pKXGβ3 was previously used to construct a ΔICP6 recombinant mutant which expresses β-Gal (Goldstein and Weller, 1988, J. Virol. 62:196–205). d33 was cotransfected with pKXGβ3 and the resulting progeny were plated on 26 cells and stained with X-gal. Blue plaques were isolated, analyzed and amplified. The resulting HSV recombinant mutant was d94 Δ(ICP4:ICP27:UL41:UL39):β-gal. All procedures were carried out as described throughout these Example Sections.

A long continuous protein labeling pattern for Vero cells and the ICP4/ICP27 complementing cell line, 26 cells, for wild type HSV (KOS) and d94 Δ(ICP4:UL41:UL39): β-gal show that wild-type levels of d94 viral gene expression are observed in 26 cells despite a restriction of d94 viral gene expression in Vero cells. This result correlates with the data obtained for the expression profile of d92 and d33 in Vero and 26 cells, as discussed in the previous Example Section.

The d94 phenotype was analyzed in noncomplementing cells. An X-gal stain of Vero cells at an m.o.i. of 0.3 PFU d94/cell at two days postinfection and three days was conducted. The lac-Z marker of d94 is abundantly expressed and Vero cell morphology is apparently unchanged relative to uninfected cells. Therefore, d94 represents an example of a non toxic HSV recombinant vector that expresses the gene of interest subsequent to target host cell infection.

Recombinant HSV vectors of the present invention show marked reduction in cytotoxicity in comparison with ICP4$^{(-)}$ mutants such as d120, which are currently being used as vectors. Cytotoxic effects are reduced by decreasing the number and type of HSV genes which are expressed subsequent to infection of the host cell, as well as inhibiting post-infection vhs functions. The survival of Vero cells as a function of m.o.i. are shown in FIG. 8. Monolayers of Vero cells were infected with d94 at the m.o.i.s listed in FIG. 12, incubated for 6 hours and then trypsinized, diluted, and plated out for colonies. At 10–14 days post infection the number of colonies were quantified and are represented as a ration to the number of colonies obtained for uninfected cells. FIG. 12 shows increased survival of Vero cells infected at high m.o.i.s with d94 in relation to d120 infected Vero cells.

Observed expression of β-gal in 32-cell mouse embryos infected with d94 demonstrates that recombinant vectors of the present invention can be used as gene transfer vectors for targeting various cell types.

10. EXAMPLE

Construction of d120IE3LAT

FIG. 5 shows a schematic drawing of the LAT/ICP0 region of d120IE3LAT, where an IE3 promoter fragment replaces the 203 bp LAT promoter fragment from −594 to −797 upstream LAT promoter region.

The IE3LAT hybrid construction was transferred to the d120 background (ICP4$^{(-)}$) and Southern blots showed that the IE3 promoter replaced the native LAT promoter at both LAT loci. d120IE3LAT grew as well as d120 on E5 (ICP4$^{(+)}$) cells, demonstrating that the IE3 insertion did not have any adverse effects on virus growth.

A northern blot of wild type (KOS), d120 and d120IE3LAT RNA hybridized against $^{32}$P-labelled probes for ICP0 and LAT was generated. FIG. 9 shows that (1) LAT is expressed in d120IE3LAT but not in d120; (2) ICP0 transcripts are greatly reduced in the d120IE3LAT background, but not in d120. Therefore, d120 expression involves an decrease in LAT expression and a concomitant increase in ICP0 expression, as discussed earlier. In contrast, replacing the LAT promoter region with the IE3 promoter at both d120 LAT loci results in an overproduction of LAT with a marked decrease in ICP0. Therefore, a reasonable conclusion is that increased LAT expression is deleterious to the accumulation of ICP0 mRNA.

A $^{35}$S-methionine labeling profile for KOS (wild-type HSV), d120 and d120IE3LAT was generated. The only difference between d120 and d120IE3LAT is that ICP0 is not evident in the d120IE3LAT profile. The levels of all other immediate early viral proteins appears unaffected. This has also been shown to be true for other immediate early mRNA transcripts. Therefore, LAT is specifically reducing ICP0 transcript and protein levels.

11. EXAMPLE

Construction of ICP27(−)/ICP4(−) Partial Peptide HSV Mutants

The data of this Example shows how interactions between ICP4 and ICP27 affect gene expression during virus infection. Viral mutants containing a complete deletion of the ICP27 gene, combined with deletions in defined functional domains of ICP4 were constructed and characterized for expression of immediate-early, early and late genes. ICP27 affects early gene expression in the absence of any ICP4 activity and ICP27 can regulate the activity of at least one domain of the ICP4 protein by affecting its ability to bind to DNA.

FIG. 7 shows the genotype of various ICP4 mutants, the ICP4 wild-type domains thought to regulate various ICP4 functions, and the level of transactivation of viral expression measured for d120, nd8-10, n208 and d8-10 in comparison to wild-type HSV (KOS). However, as discussed in Section 5.5, low levels of these ICP4$^{(-)}$ mutant peptides may promote early and late viral expression, thus impairing their use as gene transfer vehicles.

Several of these ICP4$^{(-)}$ mutant peptides were cotransfected with the ICP27$^{(-)}$ strain 5dl 1.2, on 26 cells, plaque purified and tested for an ICP27$^{(-)}$/ICP4$^{(-)}$ partial peptide, as disclosed in detail in Sections 5.1 and 7.

The construction of transformed cell lines using pSV2neo and cloned HSV genes was performed as described within this specification. The plasmid, pSV2neo, encodes the neomycin resistance gene from *E. coli* under the control of the SV40 early promoter, and confers resistance to the antibiotic G418. Approximately 4×10$^6$ Vero cells were distributed on two 85 mm petri dishes 24 h prior to transfection. 3 h prior to transfection the medium was aspirated and 10 ml of fresh medium containing 10% FBS were added. For transfection, calcium phosphate precipitates were prepared essentially as described by Graham and van der Eb, 1973, Virology 52:456–467. 1 ug of pSV2neo, 5 µg of both pK1-2 and pKHX-BH, encoding ICP4 and ICP27, respectively, and 30 µg of salmon testes DNA were suspended in 1.0 ml of 2× transfection buffer. The composition of transfection buffer was also described in Graham and van der Eb, 1973, Virology 52:456–467. 1 ml of 250 mM CaCl$_2$ was added drop-wise and the precipitate was allowed to form at room temperature for 20 min. 1 ml of suspension was then dispensed to each of the two petri dishes of Vero cells, and the cells were incubated at 37° C. for 4 h. Following this incubation, the medium was removed and 3 ml of 15% glycerol in 1× transfection buffer was added to each plate. The plates were incubated at 37° C. for 2 min, after which the glycerol was removed, the cells were washed with isotoric saline, and medium containing 10% FBS added. The cultures were incubated for 40 h at 37° C., then the cells were trypsinized and suspended in medium containing 700 ug/ml G418. The single cell suspension was plated into new 85 mm petri dishes at a density of 5×10$^3$ cells/cm$^2$, and incubated at 37° C. After 3 to 5 days the G418 concentration was lowered to 250 µg/ml, depending on the extent of cell death. G418 resistant colonies were isolated at 14 days after applying the G418 selection. Individual G418 resistant colonies were expanded in the presence of 250 ug/ml G418 by standard cell culture procedures.

Approximately 2×10$^8$ cells plated in a 60 mm dish were infected at a multiplicity of infection (m.o.i.) of 10 PFU/cell, harvested at 18 h postinfection, and lysed in buffer containing 0.6% SDS and 400 ug/ml proteinase K for 4 h at 37° C. Following RNase treatment, phenol-chloroform extractions and ethanol precipitation, equal amounts of total DNA in each sample were cleaved with the indicated restriction enzyme, fractionated by agarose gel electrophoresis, and transferred to nitrocellulose. Hybridization and the subsequent washing of the membrane were performed as previously described. The plasmids pKC-1, pKBY (cloned wt BamHI-Y fragment), and pKHX-BH were used as probes to verify the presence of mutations introduced into the viral genome. The probes were labeled with $^{32}$P using the Nick Translation System (Gibco BRL, Life Technologies) according to instructions provided by the manufacturer.

Approximately 5×10$^6$ cells seeded into 100 mm plates were infected at an m.o.i of 10 PFU/cell and harvested at the indicated times post infection. For infections performed in the presence of cycloheximide (CH), the media was supplemented with 100 ug/ml CH 1 h prior to and during infection. Total cellular RNA was extracted using the Ultraspec RNA Isolation System (Biotecx Laboratories, Inc.) as indicated by the manufacturer. Isolated RNA was resuspended in 20 µl of diethylpyrocarbonate treated water, and their concentrations were determined spectrophotometrically.

Unless otherwise indicated, 20 µg of total infected cell RNA was fractionated in 1.3% agarose formaldehyde gels containing formaldehyde with constant buffer recirculation. The conditions for blotting, hybridization and washing were described by Imbalzano, et al., 1991, J. Virol. 65:565–574. Nick-translated PKC-1 (Shepard, et al. 1991, J. Virol. 65:787–795), pW3ΔHS8 (Sacks, et al, 1987, J. Virol. 61:829–839), a gel purified 1.6 kb ScaI fragment from pKX2-βG3 (Goldstein, et al., 1988, J. Virol. 62:196–205), and a Sacd-SmaI fragment from the thymidine kinase (tk) coding region were used to detect ICP4, ICP0, ICP6 and tk messages, respectively. The probes were labeled with $^{32}$P using the Nick Translation System (Gibco BRL, Life Technologies) as described above.

Viral polypeptides were extracted (Manservigi, et al., 1977, Proc. Natl. Acad. Sci. 74:3913–3917) from cells infected at an m.o.i. of 10 PFU/cell and separated by sodium dodecyl sulfate polyacrylamide gel electrophoresis. For western blot analysis, the separated proteins were transferred to nitrocellulose by electroblotting and the blot was subsequently analyzed for the presence of ICP4 using a 1:400 dilution of N15 antibody (Shepard and DeLuca, 1991, J. Virol. 65:299–307). For detection of ICP0, the protein blots were incubated in a 1:200 dilution of N15 antibody Co25, a polyclonal rabbit raised against purified ICP0 (provided by Dr. Richard J. Courtney, The Pennsylvania State University College of Medicine, Hershey). The blots were processed with the Protoblot western blot alkaline phosphatase system (Promega) as specified by the manufacturer. For radiolabeling of viral polypeptides, approximately $6\times10^5$ cells plated in 30 m dishes were incubated with 100 $\mu$Ci/ml[$^{35}$S]-methionine for 1 h at the indicated times postinfection. The labelled viral proteins were extracted from the infected cells and separated by electrophoresis as described above.

The in vitro transcription reactions (15 $\mu$l) included 4.5 ul of Hela cell nuclear extract (approximately 60 $\mu$g protein) prepared by the method of Dignam et al. (1983, Nucl. Acids Res. 11:1475–1489), 15.7 $\mu$g/ml pL/ST plasmid as template DNA, and the following buffer components: 40 mM N-2-hydroxyethylpiperazine-n-2-ethanesulfonic acid (HEPES, pH 7.9), 60 mM KCl, 12% glycerol, 8.3 mM $MgCl_2$, 0.6 mM each of ATP, GTP, CTP and UTP, 0.3 mM dithiothreitol, and 12 units of RNasin (Promega). Where indicated, 100–150 ng of ICP4 protein were added to the reactions. The reactions were incubated at 30° C. for 80 min and stopped by the addition of 85 $\mu$l of 0.15M sodium acetate (pH 5.3) with 15 mM EDTA (pH 8.0). The reaction mixtures were extracted twice with phenol and the synthesized RNA was precipitated with ethanol prior to primer extension.

The RNA transcribed in vitro was annealed to 2–3 ng of 5'-end-labelled oligonucleotide primer that hybridizes to the transcript 75 bases from the initiation site. In a similar manner, 12 $\mu$g of total infected cell RNA was annealed to 10 ng of a $^{32}$P-end-labelled oligonucleotide primer containing the sequence from nucleotide $^+$57 to $^+$91 of the noncoding strand downstream of the L/ST promoter. DNA was 5' end-labelled by incubation in the presence of $\gamma$-[$^{32}$P]-ATP and polynucleotide kinase (New England Biolabs). Primer annealing and extension were performed as previously described by Imbalzano et al. (1991, J. Virol. 65:565–574). The primer extension products generated by the Moloney murine leukemia virus reverse transcriptase (Gibco-BRL) were analyzed by electrophoresis in 5% denaturing polyacrylamide gels. The positions of the transcription start sites were verified by running a sequencing ladder next to the primer extension products. The sequencing reactions were performed using the plasmid pKBK (cloned wt BamHI-K fragment) as template with the Sequenase version 2.0 kit (USB Technologies), as recommended by the manufacturer. Plasmid pKBK contains the joint spanning Bam HI fragment in pBR325.

The wild type (wt) and mutant ICP4 proteins in the gel retardatation assay were purified from infected cells harvested at 12–15 h postinfection. Bacterial expression and purification of recombinant (r) human TBP and TFIIB were performed as described by Kao at al. (1990, Science, 248:1646–1650) and Ha et al. (1991, Nature 352:689–695), respectively, with minor modifications (Smith, et al., 1993, J. Virol. 67:4676–4687). The 135-bp BglII-NotI fragment corresponding to nucleotide positions–110 to +25 of the pLS/T promoter was used as probe following treatment with calf intestinal alkaline phosphatase, and incubation with polynucleotide kinase and $\gamma$[$^{32}$P] ATP. The binding reactions were performed in a total volume of 30 $\mu$l containing $3.0\times10^5$ cpm (~1 ng) of probe and the indicated mixture of ICP4 proteins and general transcription factors. Where indicated, 50 ng of TBP, 500 ng of TFIIB and the indicated amount of ICP4 were added to the binding reaction. The reaction mixtures were incubated at 30° C. for 40 min in buffer conditions exactly as described by Smith et al. (1993, J. Virol. 67:4676–4687) except that 80 mM KCl was used in the reactions. DNA-protein complexes were separated on native 4% polyacrylamide gels prepared in 0.5× tris-borate-EDTA buffer (TBE), and run at 200V. After electrophoresis, the gel was dried and exposed to Kodak XAR-5 film.

The viruses d8-10, n208, and nd8-10 all contain defined ICP4 alleles and express ICP4 proteins having previously described biochemical and biological activities (DeLuca and Schaffer, 1988, J. Virol. 62:732–743), Shepard and DeLuca, 1991, J. Virol. 65:787–795, Smith, et al, 1993, J. Virol. 67:4676–4687). These are depicted in FIG. 7B along with d120. d8-10, n208, nd8-10 and d120 were each used to coinfect E26 cells with 5 d11.2 at an m.o.i. of 6 PFU/cell of each virus. At 18 h post infection, the monolayers were harvested and viral lysates were prepared. The progeny of the coinfections were plated out for plaques on E26 cells. Multiple plaques were picked from each coinfection, and freeze thawed in 0.5 ml of medium. 20 $\mu$l of each plaque isolate was screened for the ability to grow in wells of $10^5$E26, E5, E8 and Vero cells. With the exception of the d8-10:5d1.2 progeny, isolates that only grew on E26 cells were chosen for further study. For d8-10, isolates that grew only on E26 and E8 cells were chosen for further study since d8-10 does not require that ICP4 be supplied in trans to grow.

Isolates with the proper growth characteristics were used to infect $10^5$ E26 cells for the preparation of infected cell DNA. The isolated infected cell DNA was used for restriction enzyme analysis to verify the incorporation of the appropriate mutations in the genomes of the viral isolates. All of the mutations defining the ICP27 and ICP4 alleles in this study are easily assayed for by restriction enzyme and southern blot analysis. Once the identity of the desired mutant was verified, the isolates were plaque purified an additional 2 times, and then a virus stock was prepared. A final southern blot, probing for both the ICP4 and ICP27 regions of the genome was performed on all the multiple mutant isolates, wt virus, and the single mutant viruses used to construct the multiple mutants. The Nrul digest probed with the ICP27 plasmid, shows the intended viruses possess the 1.2 kb deletion characteristic of 5dl1.2. The Hpa 1 digest probed with an ICP4 -encoding plasmid (pKC1) shows the presence of the Hpa 1 site specifying the nonsense mutation in ICP4 at amino acid 774 in nd8-10, n208 and their 5 d11.2 ($\Delta$27) counterparts. As noted in this specification, d120 is deleted for 4.1 kb of ICP4 coding and 3' sequences, and has the same Hpa 1 pattern as seen in d120:$\Delta$27. The BamHI digest probed for ICP4 is diagnostic of the 204 base pair deletion defining the 8-10 mutation. The appropriately shortened Bam HI Y fragment is clearly present in both d8-10 and nd8-10. The Bam HI digest of d120 and d120:$\Delta$27 (e.g., a d92 construction) was as predicted.

The E26 cell line made it possible to obtain viruses simultaneously deficient in ICP4 and ICP27. Total yields in viral stocks range from 100 to 500 PFU per cell depending on the ICP4 allele. Therefore, standard stock titers in excess of $10^9$ PFU/ml are routinely obtained. In the case of a d120:$\Delta$27 (e.g., d92) based HSV double mutant such as d92, the viral genome lacks the flanking homology with the DNA inserted in E26 cells at the 5' end of ICP27 and at the 3' end of ICP4. This situation for the single mutants gives a frequency of appearance of wild-type virus from rescue due to growth on the cell line of $<10^{-6}$. Therefore, since rescue of each of the deletions in a mutant such as d92 should be independent events, the appearance of wild-type recombinants would be $<10^{-12}$. In practice, wild-type recombinants have never been seen.

Western blot analyses were performed on extracts from cells infected with the indicated viruses to determine if ICP4 and ICP0 levels affect later HSV gene expression.

ICP4 polypeptides of the expected sizes were observed. Comparison of each pair of mutants strains carrying a specific ICP4 allele in a wt or an ICP27 deletion background did not indicate any significant differences in the apparent sizes or levels of the ICP4 protein. The very small d120 peptide is not detected in this experiment. In addition, the levels of ICP0 polypeptides for each pair of viruses appeared similarly unaffected by the absence of ICP27.

As a preliminary assessment of changes in viral gene expression as a function of both ICP27 and specific mutant ICP4 gene products, the polypeptide profiles of the infected cells were analyzed. Vero cells infected with the indicated mutant viruses were pulse-labelled with [$^{35}$S]-methionine from 6 to 7 h postinfection, and the labelled proteins were analyzed by SDS-PAGE and autoradiography. The presence and absence of ICP27 in the n208, nd8-10 and d120 pairs is readily seen in the polypeptide profile. ICP27 is shut off at this time post infection in the KOS and d8-10 pairs and is not seen in the profiles of these mutants. Of the different ICP4 alleles tested, only the wt and d8-10 can support viral replication well into the late phase. This is evident from the polypeptide profile of cells infected with viruses carrying these alleles where the early and late gene products (ICP5, ICP8, gB, ICP25) are well-represented. Reduced expression of the late genes, most notably ICP5 and ICP25, can be observed in cells infected with the ICP4 mutant lacking the C-terminal half of the protein (n208). The presence of these proteins was barely detectable or absent in nd8-10- and d120-infected cells, consistent with previous observations.

There is a clear effect of ICP27 in all the ICP4 mutant backgrounds. Comparison of KOS and d8-10 with the corresponding viruses lacking ICP27 shows a drastic reduction in the levels of ICP5 and ICP25, consistent with ICP27 function in late HSV gene expression. The effect of ICP27 combined with the other ICP4 mutant backgrounds on early gene expression varied. At this level of resolution, the effect of ICP27 is most pronounced on ICP6. In the background of viruses expressing an ICP4 protein that has little or no activation function (nd8-10, d120), the synthesis of ICP6 was dramatically reduced at this time postinfection in the absence of ICP27. ICP27 had little effect on the accumulation of ICP6 in the n208 background, presumably because the activation function of n208 can compensate for the lack of ICP27 function. Therefore, these data indicate that ICP27 can affect the expression of genes in the absence of activation by ICP4.

The levels of accumulated mRNA transcribed from two immediate-early genes, ICP0 and ICP4, and two early genes ICP6 and the thymidine kinase gene were determined to show the effect of ICP27 on gene expression in the different ICP4 background. Total cellular RNA was isolated from infected cells 6 h postinfection and subjected to Northern blot analysis as detailed in the Materials and Methods. Replicate membranes were probed for the ICP4, ICP0, ICP6 and tk messages.

ICP27 had little effect on the accumulation of ICP4 message in any of the ICP4 mutant backgrounds. The slight reduction in ICP4 message in the d8-10-Δ27 relative to the d8-10 background is not reproducible and therefore not significant. An ICP4 message is not seen in the d120 backgrounds, due to the large deletion in the ICP4 coding sequences in these viruses. Likewise, ICP0 message abundance showed little variation as a function of ICP27. However, the more intense and broader band in the n208:Δ27, nd8-10:Δ27 backgrounds relative to their wt ICP27 counterparts is reproducible and may indicate some degree of heterogeneity in the ICP0 messages accumulated in the absence of ICP27.

The accumulation of the two early messages analyzed in this experiment, ICP6 and tk, was affected similarly by the absence of ICP27 in each of the ICP4 backgrounds. The different ICP4 alleles had relatively small effects on the level of ICP6 accumulation. It should be noted that ICP4 does have a stimulatory effect on ICP6 transcription. The level of ICP6 seen in d120 was about 4-fold lower than that seen in KOS infected cells. Deletion of ICP27 in each of the ICP4 backgrounds resulted in the relative reduction in the levels of ICP6 message. The most pronounced reductions were seen in the nd8-10 and d120 pairs of viruses. Surprisingly, in the absence of ICP27 in these backgrounds, the level of ICP6 message is barely detectable (lanes 8 and 10). This is notable since ICP0 is abundantly expressed and localized to the nucleus in the nd8-10:Δ27, and d120: Δ27 backgrounds. The same general trend is seen for the tk message. The only difference between tk and ICP6 is that while ICP6 is induced approximately 3–4 fold by ICP4, tk is induced 30- to 40-fold. This is likely due to differences in the basal promoter strength of the two promoters.

To more accurately evaluate the effect of ICP27 on the levels of tk message synthesized by viruses carrying defective alleles of ICP4, a separate blot analysis was carried out where the sensitivity of detection was increased. This was accomplished by loading about three-fold more RNA in each lane and exposing the autoradiogram longer. The ratio of tk message in n208 and n208:Δ27, approximates the ratios observed for the virus pairs KOS and KOS:Δ27 and d8-10 and d8-10:Δ27 infected cells represents a 10 to 12 fold reduction from that seen in nd8-10 and d120 infected cells, respectively. To rule out the possibility that the differences in the levels of tk message were due to gross variations in the amount of input viruses, RNA from cells infected in the presence of cycloheximide was analyzed. Infections with the different viruses were performed at the same multiplicities of infection used with the untreated cells. In the absence of protein synthesis, the different viruses were expected to express the tk message at similar levels. Minor variations were observed, but these differences were not sufficient to account for the differences seen in the absence of cycloheximide.

Expression of tk in the presence of cycloheximide is presumably comparable to its expression in the absence of ICP4 and ICP27, as well as other immediate early functions. The results show that under these conditions, it is still expressed albeit at very low levels. However, in the absence of ICP4 activation function, ICP27 has a significant effect on the levels of ICP6 and tk mRNA accumulation. To examine the effect of ICP27 on the repression function of the ICP4 peptides synthesized in the different backgrounds, expression levels of a gene which is normally repressed by ICP4 was determined. Such a gene, L/ST, belongs to a family of transcripts spanning the junction between the long and short unique regions of the HSV-1 genome (Su and Knipe, 1989, Virology 170:496–504). The L/STs are expressed late in infection from a promoter that achieves maximum activity only in the absence of functional ICP4. The promoter contains the VP16 recognition sequence characteristic of immediate early regulatory regions, an array of Sp1-binding sites, a TATA box, and a high affinity ICP4 binding site (FIG. 10A), which is responsible for its repression.

To explore the regulatory role of ICP4 on the expression of the L/STs and the possible effect of ICP27 on this specific ICP4 function, synthesis of the L/STs in cells infected with the mutant viruses by primer extension was assayed. Low levels of L/ST accumulation was seen in the KOS and d8-10 backgrounds at 12 h postinfection, which were not seen with there $\Delta 27$ counterparts. This is consistent with low level accumulation of L/ST during the late phase of infection (Wilcox, et al., 1980, J. Virol. 33:167–182). In the absence of ICP4, with or without the additional deletion of ICP27, the accumulation of L/ST was clearly evident. The multiple bands corresponding to the primer extension products represent transcripts initiated from three alternative transcription start sites, with the major site being the same as reported (Yeh, et al., 1993, J. Virol. 67:7373–7382). Repression of the L/ST promoter was observed with the virus carrying the n208 allele of ICP4 regardless of the presence or absence of ICP27. As with n208, repression of the promoter was also observed with the nd8-10 virus. In the nd8-10:$\Delta 27$ background, repression was relieved, This observation suggests that ICP27 affects the ability of the nd8-10 mutant ICP4 protein to repress transcription of the L/ST promoter.

In vitro transcription experiments using the L/ST promoter as template were conducted to determine if the differential effect on L/ST repression in the nd8-10 backgrounds was a direct reflection of altered activity of the nd8-10 protein. The activity of the promoter was repressed by ICP4 purified from wt-infected cells. Repression of LIST was also observed with the nd8-10 ICP4. In contrast, the ICP4 protein synthesized in nd8-10:$\Delta 27$ infected cells was no longer able to repress the L/ST promoter. This result indicates that although the two viruses code for the same ICP4 protein, the mutant ICP4 protein synthesized by nd8-10 is biochemically distinct from that expressed by nd8-10:$\Delta 27$.

To determine why nd8-10:$\Delta 27$ ICP4 was not able to repress transcription, we compared the mutant ICP4 proteins made in nd8-10 and nd8-10:$\Delta 27$ infected cells with respect to two properties of ICP4 that contribute to its repression activity: (1) the ability to bind to the ICP4 binding site, and (2) the ability to form a tripartite complex with TBP and TFIIB on the promoter. A segment of the L/ST promoter containing the ICP4 binding site and TATA box was used as probe for the gel retardation assays. Like the wild-type protein, the mutant ICP4 protein made by the nd8-10 virus binds to DNA and can participate in a tripartite complex formation with TPB and TFIIB as evidenced by the formation of a slower migrating complex in the presence of TBP and TFIIB.On the other hand, the same protein made in the absence of ICP27 (by the virus nd8-10:$\Delta 27$) is defective for DNA binding and consequently, the formation of tripartite complexes (FIG. 21C). While the amounts of the nd8-10 and nd8-10:$\Delta 27$ proteins used in the reactions was approximately equal binding activity of a given amount of the nd8-10 protein (20 ng) was compared to increasing amounts of the nd8-10:$\Delta 27$ protein to more rigorously control for small variations in the amounts of the proteins, and also to see if nd8-10:$\Delta 27$ ICP4 could engage in tripartite complexes if enough if the protein bound to DNA. Small amounts of the nd8-10:$\Delta 27$ protein could be seen binding to the probe and forming tripartite complexes when 40 ng, and more evidently, 80 ng of ICP4 protein were included in the binding reactions. However, despite increasing the amount of protein used in the binding reactions by 4-fold, the amount of nd8-10:$\Delta 27$ protein observed binding to the probe was dramatically less than the amount of nd8-10 that bound.

These expermiments indicate that the nd8-10 protein can repress L/ST transcription, but does not have this activity when expressed in viral infection in the absence of ICP27. This is presumably due to an as yet unknown modification of the ICP4 protein that directly or indirectly involves ICP27, and renders the nd8-10 protein deficient in DNA binding.

Therefore, HSV strains deleted for ICP27 in combination with a partial ICP4 mutants, preferably including comprising a deletion within the 5' and/or 3' transactivation domain of wild-type ICP4, may be used alone or in combination with other HSV mutant strains disclosed within this specification to construct various HSV-based gene transfer vectors.

13. Deposit of Microorganisms

The following ICP4ICP27 complementing cell line and HSV-1 ICP4$^{(-)}$ICP27$^{(-)}$ mutant strain were deposited with the American Type Culture Collection (ATCC), 12301 Parklawn Drive, Rockville, Md. 20852, on Apr. 21, 1993, and assigned accession numbers as follows:

| | Accession No. |
|---|---|
| Cell line "26 cells" | CRL 11332 |
| HSV-1 strain "d92" | VR 2406 |

Whereas particular embodiments of the invention has been described hereinbefore, for purposes of illustration, it would be evident to those skilled in the art that numerous variations of the details may be made without departing from the invention as defined in the appended claims.

What is claimed is:

1. A recombinant HSV vector comprising genomic mutations within the ICP4 and ICP27 genes such that an ICP4 gene product and an ICP27 gene product is defective.

2. The recombinant HSV vector of claim 1, comprising at least one genomic mutation within an additional HSV gene such that an additional HSV gene product is defective.

3. The recombinant HSV vector of claim 1, which can be propagated in the absence of a helper virus.

4. The recombinant HSV vector of claim 2, wherein a genomic mutation is within a nonessential HSV gene.

5. The recombinant HSV vector of claim 2, wherein a genomic mutation is within the UL41 gene.

6. The recombinant HSV vector of claim 2, wherein a genomic mutation is within the UL39 gene.

7. The recombinant HSV vector of claim 2, comprising at least one genomic mutation within an additional HSV gene such that an additional HSV gene product is defective.

8. The recombinant HSV vector of claim 7, wherein a genomic mutation is within the UL41 gene and wherein a genomic mutation is within the UL39 gene.

9. The recombinant HSV vector of claim 7, comprising genomic mutations within all HSV immediate early genes such that any expressed HSV immediate early gene product is defective.

10. The recombinant HSV vector of claim 7, wherein a genomic mutation is within the ICP22 gene.

11. The recombinant HSV vector of claim 7, wherein genomic mutations are within the ICP22 and UL41 genes.

12. A recombinant HSV vector, which comprises:
a) a genomic mutation in at least the ICP4 gene such that an ICP4 gene product is defective; and
b) an exogenous promoter positively controlling expression of latency associated transcripts within an ICP4$^{(-)}$ genomic background.

13. The recombinant HSV vector of claim 12, wherein said exogenous promoter replaces a portion of the HSV genome from about −594 bp to about −797 bp 5' of said latency associated transcript.

14. The recombinant HSV vector of claim 12, wherein said exogenous promoter is the IE3 promoter.

15. The recombinant HSV vector of claim 12, which expresses a latency associated transcript in non-neuronal cells.

16. The recombinant HSV vector of claim 12, further comprising a genomic mutation in the ICP27 gene such that an expressed ICP27 gene product is defective.

17. The recombinant HSV vector of claim 12, further comprising a genomic mutation in the UL41 gene such that an expressed UL41 gene product is defective.

18. The recombinant HSV vector of claim 12, further comprising a genomic mutation in the UL39 gene such that an expressed UL39 gene product is defective.

19. The recombinant HSV vector of claim 12, which can be propagated in the absence of a helper virus.

20. The recombinant HSV vector of claim 16, which expresses a latency associated transcript in non-neuronal cells.

21. The recombinant HSV vector of claim 16, wherein said exogenous promoter replaces a portion of the HSV genome from about −594 bp to about −797 bp 5' of said latency associated transcript.

22. The recombinant HSV vector of claim 16, wherein said exogenous promoter is the IE3 promoter.

23. The recombinant HSV vector of claim 17, which expresses a latency associated transcript in non-neuronal cells.

24. The recombinant HSV vector of claim 17, wherein said exogenous promoter replaces a portion of the HSV genome from about −594 bp to about −797 bp 5' of said latency associated transcript.

25. The recombinant HSV vector of claim 17, wherein said exogenous promoter is the IE3 promoter.

26. The recombinant HSV vector of claim 18, wherein said exogenous promoter replaces a portion of the HSV genome from about −594 bp to about −797 bp 5' of said latency associated transcript.

27. The recombinant HSV vector of claim 18, wherein said exogenous promoter is the IE3 promoter.

28. The recombinant HSV vector of claim 18, which expresses a latency associated transcript in non-neuronal cells.

29. A recombinant HSV vector, which comprises:
a) a genomic mutation in at least the ICP4 gene such that an ICP4 gene product is defective; and
b) an exogenous promoter positively controlling expression of latency associated transcripts within an ICP4$^{(-)}$ genomic background; and
c) at least one exogenous DNA coding region under transcriptional control of a promoter.

30. The recombinant HSV vector of claim 29, which can be propagated in the absence of a helper virus.

31. The recombinant HSV vector of claim 29, wherein said exogenous promoter replaces a portion of the HSV genome from about −594 bp to about −797 bp 5' of said latency associated transcript.

32. The recombinant HSV vector of claim 29, wherein said exogenous promoter is the IE3 promoter.

33. The recombinant HSV vector of claim 29, which expresses a latency associated transcript in non-neuronal cells.

34. The recombinant HSV vector of claim 29, further comprising a genomic mutation in the ICP27 gene such that an expressed ICP27 gene product is defective.

35. The recombinant HSV vector of claim 29, further comprising a genomic mutation in the UL41 gene such that an expressed UL41 gene product is defective.

36. The recombinant HSV vector of claim 29, further comprising a genomic mutation in the UL39 gene such that an expressed UL39 gene product is defective.

37. A recombinant HSV vector, comprising:
a) a genomic mutation within the ICP27 gene such that an ICP27 gene product is defective; and
b) a mutation in the ICP4 gene such that an ICP4 mutant gene product shows altered transactivation of early HSV genes.

38. The recombinant HSV vector of claim 37, wherein said ICP4 gene mutation comprises a deletion within the 5' transactivation domain of the ICP4 protein.

39. The recombinant HSV vector of claim 37, wherein said ICP4 gene mutation comprises a deletion within the 5' transactivation domain and a deletion within the 3' transactivation domain of the ICP4 protein.

40. The recombinant HSV vector of claim 37, wherein said ICP4 mutant gene product retains functional ICP4 repressor activity.

41. The recombinant HSV vector of claim 37, which can be propagated in the absence of a helper virus.

42. The recombinant HSV vector of claim 38, wherein said ICP4 gene mutation comprises a deletion within the 3' transactivation domain of the ICP4 protein.

43. The recombinant HSV vector of claim 38, wherein said ICP4 gene mutation comprises a deletion from about 135 bp to about 200 bp from the initiating ATG of the ICP4 gene.

44. The recombinant HSV vector of claim 38, wherein said ICP4 mutant gene product retains functional ICP4 repressor activity.

45. The recombinant HSV vector of claim 42, wherein said ICP4 gene mutation comprises a deletion from about 800 bp to about 1300 bp from the initiating ATC 3' of the ICP4 gene.

46. A recombinant HSV vector, which comprises:
a) a genomic mutation within the ICP27 gene such that an ICP27 gene product is defective;
b) a mutation in the ICP4 gene such that an ICP4 mutant gene product shows altered transactivation of early HSV genes; and
c) at least one exogenous DNA coding region under transcriptional control of a promoter.

47. The recombinant HSV vector of claim 46, which can be propagated in the absence of a helper virus.

48. The recombinant HSV vector of claim 46, wherein said ICP4 gene mutation comprises a deletion within the 5' transactivation domain of the ICP4 protein.

49. The recombinant HSV vector of claim 46, wherein an expressed ICP4 mutant gene product retains functional ICP4 repressor activity.

50. A recombinant HSV vector comprising genomic mutations within the ICP4 and ICP27 genes such that at least an ICP4 gene product and an ICP27 gene product is defective and comprising at least one exogenous DNA coding region under transcriptional control of a promoter.

51. The recombinant HSV vector of claim 50 comprising at least one genomic mutation within an additional HSV gene such that an additional HSV gene product is defective.

52. The recombinant HSV vector of claim 50, wherein said exogenous DNA coding region and promoter(s) are contained within one or more nonmutated, nonessential region(s) of said HSV genome.

53. The recombinant HSV vector of claim 48, which can be propagated in the absence of a helper virus.

54. The recombinant HSV vector of claim 51, wherein a genomic mutation is within a nonessential HSV gene.

55. The recombinant HSV vector of claim 51, wherein a genomic mutation is within the UL41 gene.

56. The recombinant HSV vector of claim 51, wherein a genomic mutation is within the UL39 gene.

57. The recombinant HSV vector of claim 51, further comprising at least one genomic mutation within an additional HSV gene such that an additional HSV gene product is defective.

58. The recombinant HSV vector of claim 51, wherein a genomic mutation is within the ICP22 gene.

59. The recombinant HSV vector of claim 51, wherein genomic mutations are within the ICP22 and UL41 genes.

60. The recombinant HSV vector of claim 57, wherein a genomic mutation is within the UL41 gene and the UL39 gene.

61. The recombinant HSV vector of claim 57, comprising genomic mutations within all HSV immediate early genes such that any expressed HSV immediate early gene is defective.

62. The recombinant HSV vector of claim 52, wherein said exogenous DNA coding region and promoter(s) are contained within at least a portion of the UL39 gene.

63. The recombinant HSV vector of claim 34, which expresses a latency associated transcript in non-neuronal cells.

64. The recombinant HSV vector of claim 34, wherein said exogenous promoter replaces a portion of the HSV genome from about −594 bp to about −797 bp 5' of said latency associated transcript.

65. The recombinant HSV vector of claim 34, wherein said exogenous promoter is the IE3 promoter.

66. The recombinant HSV vector of claim 35, which expresses a latency associated transcript in non-neuronal cells.

67. The recombinant HSV vector of claim 35, wherein said exogenous promoter replaces a portion of the HSV genome from about −594 bp to about −797 bp 5' of said latency associated transcript.

68. The recombinant HSV vector of claim 35, wherein said exogenous promoter is the IE3 promoter.

69. The recombinant HSV vector of claim 36, wherein said exogenous promoter replaces a portion of the HSV genome from about −594 bp to about −797 bp 5' of said latency associated transcript.

70. The recombinant HSV vector of claim 36, wherein said exogenous promoter is the IE3 promoter.

71. The recombinant HSV vector of claim 36, which expresses a latency associated transcript in non-neuronal cells.

72. The recombinant HSV vector of claim 48, wherein said ICP4 gene mutation comprises a deletion within the 3' transactivation domain of the ICP4 protein.

73. The recombinant HSV vector of claim 48, wherein said ICP4 gene mutation comprises a deletion within the 5' transactivation domain and a deletion within the 3' transactivation domain of the ICP4 protein.

74. The recombinant HSV vector of claim 72, wherein said ICP4 gene mutation comprises a deletion from about 800 bp to about 1300 bp from the initiating ATC 3' of the ICP4 gene.

75. The recombinant HSV vector of claim 73, wherein said ICP4 gene mutation comprises a deletion from about 135 bp to about 200 bp from the initiating ATG of the ICP4 gene.

76. The recombinant HSV vector of claim 73, wherein an expressed ICP4 mutant gene product retains functional ICP4 repressor activity.

* * * * *

UNITED STATES PATENT AND TRADEMARK OFFICE
CERTIFICATE OF CORRECTION

PATENT NO. : 5,879,934
DATED : March 9, 1999
INVENTOR(S) : DeLuca, Neal A.

It is certified that errors appear in the above-identified patent and that said Letters Patent is hereby corrected as shown below:

In Column 3, line 7: "ICP6may" should read --ICP6 may--

In Column 3, line 57: "a" should read --an--

In Column 4, line 25: "a" should read --an--

In Column 4, line 35: "a" should read --an--

In Column 4, line 56: "in trans" should read --*in trans*--

In Column 5, line 14: "(CP4" should read --(ICP4--

In Column 5, line 49: "in vitro" should read --*in vitro*--

In Column 8, line 29: "FIG. 9" should read --FIG. 7--

In Column 10, line 20: "Althohugh" should read --Although--

In Column 10, lines 64 and 65: "in cis" should read --*in cis*--

In Column 11, line 66: "A a long" should read --A long--

In Column 12, line 40: "(data not shown)" should be deleted

In Column 13, line 18: "Given" should begin a new paragraph

UNITED STATES PATENT AND TRADEMARK OFFICE
CERTIFICATE OF CORRECTION

PATENT NO. : 5,879,934
DATED : March 9, 1999
INVENTOR(S) : DeLuca, Neal A.

It is certified that errors appear in the above-identified patent and that said Letters Patent is hereby corrected as shown below:

In Column 13, line 58: "he" should read --the--

In Column 14, line 12: "ICP6being" should read --ICP6 being--

In Column 16, line 7: "an" should be deleted

In Column 18, line 4: --These methods are unique in that a novel ICP4ICP27 complementing cell line is used. By use of the novel cell line the ICP4$^{(-)}$ICP27$^{(-)}$ nonessential gene$^-$ HSV strain can be generated, regardless of how much the growth of the novel strain is dampened due to incorporation of deletions or inactivating mutations in nonessential viral genes.

It will be appreciated that the present invention encompasses any method to generate ICP4$^{(-)}$ICP27$^{(-)}$ nonessential gene(s)$^-$ HSV strains which use an ICP4ICP27 complementing cell line.-- should be inserted after "together" as two paragraphs In Column 19, line 36: "nec$^r$" should read --neo$^r$--

In Column 20, line 4: "in vivo" should read --*in vivo*--

In Column 20, line 5: "in vitro" should read --*in vitro*--

In Column 21, line 26: "plated plated" should read --plated--

UNITED STATES PATENT AND TRADEMARK OFFICE
CERTIFICATE OF CORRECTION

PATENT NO.  : 5,879,934
DATED       : March 9, 1999
INVENTOR(S) : DeLuca, Neal A.

It is certified that errors appear in the above-identified patent and that said Letters Patent is hereby corrected as shown below:

In Column 22, line 27: "show" should read --shows--

In Column 22, line 48: "FIG. 12" should read --FIG. 8--

In Column 22, line 53: "FIG. 12" should read --FIG. 8--

In Column 23, line 67: "ug" should read --µg--

In Column 24, lines 17, 23, 28, and 45: "ug" should read --µg--

In Column 24, line 61: "ICP6and" should read --ICP6 and--

In Column 25, line 19: "in vitro" should read --*in vitro*--

In Column 25, line 57: "retardatation" should read --retardation--

In Column 26, line 18: "FIG. 7B" should read --FIG. 6B--

In Column 26, line 31: "in trans" should read --*in trans*--

In Column 26, line 43: "southern" should read --Southern--

In Column 27, line 49: "ICP6was" should read --ICP6 was--

UNITED STATES PATENT AND TRADEMARK OFFICE
CERTIFICATE OF CORRECTION

PATENT NO.   : 5,879,934
DATED        : March 9, 1999
INVENTOR(S)  : DeLuca, Neal A.

It is certified that errors appear in the above-identified patent and that said Letters Patent is hereby corrected as shown below:

In Column 27, lines 59 and 65: "ICP6and" should read --ICP6 and--

In Column 28, line 13: "ICP6and" should read --ICP6 and--

In Column 28, line 16: "ICP6accumulation" should read --ICP6 accumulation--

In Column 28, line 17: "ICP6transcription" should read --ICP6 transcription--

In Column 28, line 18: "ICP6seen" should read --ICP6 seen--

In Column 28, line 28: "ICP6is" should read --ICP6 is--

In Column 28, line 30: "basal promoter strength" should read --basal strength--

In Column 28, line 59: "ICP6and" should read --ICP6 and--

In Column 29, line 5: "10A)" should read --10--

In Column 29, line 12: "there" should read --their--

In Column 29, line 29: "In vitro" should read --*in vitro*--

In Column 29, line 34: "LIST" should read --L/ST--

In Column 29, line 58: "(FIG. 21C)" should be deleted

UNITED STATES PATENT AND TRADEMARK OFFICE
CERTIFICATE OF CORRECTION

PATENT NO. : 5,879,934
DATED : March 9, 1999
INVENTOR(S) : DeLuca, Neal A.

It is certified that errors appear in the above-identified patent and that said Letters Patent is hereby corrected as shown below:

In Claim 53, Column 33, line 8: "48" should read --50--

Signed and Sealed this

Twenty-sixth Day of October, 1999

Attest:

Attesting Officer

Q. TODD DICKINSON

Acting Commissioner of Patents and Trademarks